US011020439B2

(12) United States Patent
Isohama et al.

(10) Patent No.: US 11,020,439 B2
(45) Date of Patent: Jun. 1, 2021

(54) HONEY FRACTION

(71) Applicants: Yamada Bee Company, Inc., Okayama (JP); Tokyo University of Science Foundation, Tokyo (JP)

(72) Inventors: Yoichiro Isohama, Tokyo (JP); Ichiro Horie, Tokyo (JP); Hiroko Tani, Okayama (JP); Yuka Kimura, Okayama (JP); Maiko Yoshimatsu, Okayama (JP); Tae Nakatsuka, Okayama (JP)

(73) Assignee: YAMADA BEE COMPANY, INC., Okayama (JP)

( * ) Notice: Subject to any disclaimer, the term of this patent is extended or adjusted under 35 U.S.C. 154(b) by 504 days.

(21) Appl. No.: 15/577,305

(22) PCT Filed: May 19, 2016

(86) PCT No.: PCT/JP2016/064930
§ 371 (c)(1),
(2) Date: Nov. 27, 2017

(87) PCT Pub. No.: WO2016/194638
PCT Pub. Date: Dec. 8, 2016

(65) Prior Publication Data
US 2018/0147244 A1    May 31, 2018

(30) Foreign Application Priority Data

May 29, 2015   (JP) .............................. JP2015-110057

(51) Int. Cl.
| *A61K 35/644* | (2015.01) |
| *A61K 35/63* | (2015.01) |
| *A61P 25/04* | (2006.01) |
| *A61P 11/14* | (2006.01) |
| *A61P 11/00* | (2006.01) |
| *B01J 20/286* | (2006.01) |

(52) U.S. Cl.
CPC ............ *A61K 35/644* (2013.01); *A61K 35/63* (2015.01); *A61P 11/00* (2018.01); *A61P 11/14* (2018.01); *A61P 25/04* (2018.01); *B01J 20/286* (2013.01)

(58) Field of Classification Search
None
See application file for complete search history.

(56) References Cited

U.S. PATENT DOCUMENTS

2014/0274931 A1    9/2014   Kato et al.

FOREIGN PATENT DOCUMENTS

| JP | H06128287 A | 5/1994 |
| JP | 2002-518057 A | 6/2002 |
| JP | 2002-529477 A | 9/2002 |
| JP | 2005-112785 A | 4/2005 |
| JP | 2008-501361 A | 1/2008 |
| JP | 2008/061531 A | 3/2008 |
| JP | 2013-503624 A | 2/2013 |
| JP | 2014-515724 A | 7/2014 |
| WO | WO 99/67408 A1 | 12/1999 |
| WO | WO 00/28064 A1 | 5/2000 |
| WO | WO 2005/120250 A1 | 12/2005 |
| WO | WO 2011/027290 A1 | 3/2011 |
| WO | WO 2012/087160 A2 | 6/2012 |
| WO | WO 2013/061816 A1 | 5/2013 |

OTHER PUBLICATIONS

Moreira, R.F.A., et al: "Flavor composition of cashew (*Anacardium occidentale*) and Marmeleiro (*Croton* species) Honeys", J. Agr Food Chem 2002, vol. 50, pp. 7616-7621.
Communication under Rule 62 EPC, extended European search report dated Jan. 9, 2019 for European Patent Application No. 16803073.2, 9 pages.
Bogdanov, Stefan, "Nature and origin of the antibacterial substances in honey", LWT—Food Science and Technology, Academic Press UK, Jan. 1, 1997, vol. 30, No. 7, pp. 748-753.
Morales, V., et al, "Rapid separation on activated charcoal of high oligosaccharides in honey", Chromatographia: An International Journal for Rapic Communication in Chromatography, Electrophoresis and Associated Techniques, Vieweg Verlag, WI, Jul. 20, 2006, vol. 64, No. 3-4, pp. 1-6.
Owoyele, Bamidele Victor, et al, "Analgesic and anti-inflammatory effects of honey: the involvement of autonomic receptors", Metabolic Brain Disease, Dec. 10, 2013, vol. 29, No. 1, pp. 167-173.
White, Jonathan W., et al, "Composition of Honey. IV. Identification of the Disaccharides", Archives of Biochemistry and Biophysics, Academic Press US, Feb. 1, 1959, vol. 80, No. 2, pp. 386-392.
International Search Report for PCT/JP2016/064930, dated Jul. 12, 2016, 2 pages.
International Preliminary Report on Patentability for PCT/JP2016/064930, dated Dec. 7, 2017, 10 pages.
Muraki, Masato, "Clinical Study on Cough", Med J Kinki Univ, vol. 35, No. 3,4, 2010, pp. 145-149.
Paul, Ian M., et al., "Effect of Honey, Dextromethorphan, and No Treatment on Nocturnal cough and sleep quality for coughing children and their parents", Archives of pediqatrics adolescent medicinie, vol. 161, No. 12, Dec. 2007, pp. 1140-1146.
Paul, Ian M., "Therapeutic options for acute cough due to upper respiratory infections in children", Lung Sep. 4, 2011, vol. 190, pp. 41-44.

(Continued)

*Primary Examiner* — Michael Barker
(74) *Attorney, Agent, or Firm* — Squire Patton Boggs (US) LLP

(57) ABSTRACT

The present invention provides a honey fraction obtainable by a method comprising (a) obtaining an absorbed component by causing honey to be brought into contact with an adsorbent, (b) obtaining an organic solvent fraction by eluting the absorbed component with an organic solvent that is acetone, ethyl acetate, or ethanol, and (c) obtaining a honey fraction from the organic solvent fraction.

8 Claims, 15 Drawing Sheets

(56) References Cited

OTHER PUBLICATIONS

Sugii, Shinji, "Tokushu Mitsubachi Yurai Genryo—sono Genjo to Oyo no Jissai", Fragrance Journal 2002, vol. 30, No. 3, pp. 11-16, p. 15 right col., 4$^{th}$ paragraph.

Takahama, Kazuo, et al., "Cough-Diversity and the peripheral mechanisms of production", Folia Pharmacol Jpn 105, 1995, pp. 41-52.

Uetake, Saori, et al., "Pharmacological Study on Antitussive Effect of Honey", Pharmacometrics Oct. 2014, vol. 87, No, 1/2, p. 56.

Yamaguchi, Shigeki, "Mechanism of action of opioid analgesic agents", Anet, vol. 18, No. 3, 2014, pp. 12-15.

Moreira, et al, "Flavor Composition of Cashew (*Anacardium occidentale*) and Marmeleiro (*Croton* Species) Honeys", Journal of Agricultural and Food Chemistry 2002; Nov. 15, 2002; vol. 50, pp. 7616-7621.

Wenling, Mao "Study on Constituents from Propolis and Honey", A Dissertation submitted to the Graduate School of Henan University in Partial Fulfillment of the Requirements for the Degree of Master of Science Jun. 2011, 75 pages, Abstract pp. 6-7.

(a)

(b)

(c)

HONEY FRACTION

TECHNICAL FIELD

The present invention relates to a honey fraction.

BACKGROUND ART

It is suggested that honey may exhibit effectiveness against cough symptoms caused by cold in an infant (Non-Patent Literature 1). As a mechanism, secretomotor of saliva or mucus of an airway by honey's sweetness is presumed, but it has not been clarified yet (Non-Patent Literature 2).

Cough is one of the mechanisms of reflex for removing foreign matters or secretions of the airway, which is caused by inflammatory changes and/or structural changes in the airway, or inhalation of chemical and/or physical irritants. As a cough receptor, a rapidly adapting receptor (RARs) existing in Aδ-fiber and a C-fiber receptor have been known. When stimulation is added to these cough receptors, cough is caused through an afferent path of superior laryngeal nerve and vagus nerve (Non-Patent Literature 3).

Examples of an antitussive agent include a central narcotic antitussive agent and a non-narcotic antitussive agent, and also include peripheral antitussive agents such as a bronchodilator, an expectorant, an anti-pathogenic microorganism, an anti-allergic agent, an anti-IgE antibody, steroid, and Chinese medicine.

CITATION LIST

Patent Literature

Non Patent Literature

[Non-Patent Literature 1] Ian M. Paul, Therapeutic Options for Acute Cough Due to Upper Respiratory Infections in Children, Lung, 190 (1), 41-44, (2012).

[Non-Patent Literature 2] Ian M. Paul, et. al, Effect of Honey, Dextromethorphan, and No Treatment on Nocturnal Cough and Sleep Quality for Coughing Children and Their Parents, Archives of pediatrics adolescent medicine, 161 (12), 1140-1146 (2007).

[Non-Patent Literature 3] Masato Muraki, et al., Clinical cough, Kinki University medical journal, Vol. 35 (No. 3 and 4), Pages 145 to 149, 2010

[Non-Patent Literature 4] Kazuo Takahama, et al., Cough—its diversity and peripheral mechanisms, Japanese Pharmacology, 105, Pages 41 to 52, 1995

SUMMARY OF INVENTION

Technical Problem

While having a strong effect to lower central excitement on cough, the narcotic antitussive agent has side effects such as nausea, vomiting, respiratory depression, constipation, drowsiness, dysuria, dependency, and drug resistance, and has a weak suppression effect on the cough at the time of airway inflammation. On the other hand, the non-narcotic antitussive agent generally has weak effect and it has side effects such as dizziness, dry mouth, drowsiness, anorexia, constipation, and tachycardia, though it has no side effects such as dependency and respiratory depression. The peripheral antitussive agent blocks an afferent path that delivers the stimulation of the cough or a distal path that delivers the excitement from the center with peripheries (airway, lung, respiratory muscle, and the like), but in many cases, the improvement is not sufficiently achieved even after treatment of causative diseases (Non-Patent Literatures 3 and 4). Development of the antitussive agent which is excellent in effectiveness and safety as compared with existing agents has been required.

An object of the present invention is to provide a honey fraction having an excellent antitussive action.

Solution to Problem

The present invention provides a honey fraction which is obtainable by a method comprising (a) obtaining an adsorbed component by causing honey to be brought into contact with an adsorbent, (b) obtaining an organic solvent fraction by eluting the absorbed component with an organic solvent that is acetone, ethyl acetate, or ethanol, and (c) obtaining a honey fraction from the organic solvent fraction. The honey fraction has an excellent antitussive action.

The absorbed component eluted in Step (b) is preferably a component which is not eluted with water or methanol. With this, the honey fraction which can be obtained with the method can be made to have higher antitussive activity. In addition, the organic solvent is preferably acetone.

It is preferable that the method further comprises removing a component which is elutable with water from the absorbed component before Step (b). In addition, it is preferable that the method further comprises removing a component which is elutable with methanol, a methanol aqueous solution, or an ethanol aqueous solution from the absorbed component before Step (b).

It is preferable that Step (b) further comprises at least one step selected from the group consisting of the following Step (b-1), Step (b-2), and Step (b-3).

(b-1) a step of obtaining, as the organic solvent fraction, a fraction which has a spot at a Rf value in a range of 0.49 to 0.55, which is colored with an anisaldehyde sulfuric acid reagent (heated at 105° C. after spraying) and a spot at a Rf value in a range of 0.56 to 0.62, which is less colored than the aforementioned spot when the absorbed component eluted with the organic solvent is fractionated by an elution time, and is developed with a solvent in which a mixing ratio of hexane/ethyl acetate is 4/1 in a thin layer chromatography using silica gel, (b-2) a step of obtaining, as the organic solvent fraction, a fraction which has spots at a Rf value 0, and in a range of 0.54 to 0.94, which are colored with a doragendorf reagent when the absorbed component eluted with the organic solvent is fractionated by the elution time, and is developed with a solvent in which the mixing ratio of chloroform/methanol/acetate is 9/1/1 in the thin layer chromatography using silica gel (b-3) a step of obtaining, as the organic solvent fraction, a fraction which is detected with a retention time in a range of 2.0 to 4.0 minutes, and has a peak which has molecular ion peaks of m/z438 [M+H] and m/z436 [M−H] in a case where the absorbed component eluted with the organic solvent is fractionated by the elution time, and is measured under the following conditions in liquid chromatography mass spectrometry

Measuring Conditions

Column: Acquity UPLC BFH C18 (φ2.1×100 mm, manufactured by Waters Corporation)
Flow rate: 0.4 mL/min
Column temperature: 40° C.

Solvent: 5% B (0 to 0.25 min), 5 to 100% B (0.25 to 10 min, linear gradient), 100% B (10 to 12 min), 5% B (12 to 15 min)

A: 0.05% of formic acid aqueous solution, B: 100% of acetonitrile

Injection volume: 2 μl

Step (b) preferably further comprises Step (b-4). Step (b-4) is a step of obtaining, as the organic solvent fraction, a fraction which satisfies at least one condition of the following conditions (1) and (2) by further fractioning the fraction obtained in Step (b-2) with a reverse phase adsorbent.

(1) Having a spot at a Rf value in a range of 0 to 0.22 which is colored with a doragendorf reagent when the development is performed with a solvent in which the mixing ratio of chloroform/methanol/acetate is 9/1/0.3 in the thin layer chromatography using silica gel (2) Having at least one spot selected from the group consisting of the spots at Rf values in a range from 0.02 to 0.09, 0.10 to 0.20, and 0.30 to 0.53, which is colored with a ninhydrin reagent (heated at 105° C. after spraying) when the development is performed with a solvent in which the mixing ratio of chloroform/methanol/water is 1/1/0.3 in the thin layer chromatography using silica gel In addition, according to the present invention, there is provided a honey fraction obtainable by a method comprising (d) causing honey to be brought into contact with an acid adsorbent so as to obtain an absorbed component which is absorbed to the acid adsorbent by, (e) obtaining a basic aqueous solution fraction by eluting the absorbed component with the basic aqueous solution, and (f) obtaining a honey fraction from the basic aqueous solution fraction, or a method comprising (d') causing honey to be brought into contact with a basic adsorbent so as to obtain an absorbed component which is adsorbed to the basic adsorbent (e') obtaining an acidic aqueous solution fraction by eluting the absorbed component with an acidic aqueous solution, and (f') obtaining a honey fraction from the acidic aqueous solution fraction.

Further, according to the present invention, there is provided an opioid activator comprising the honey fraction as an active component. Further, according to the present invention, there is provided an antitussive agent or an analgesic agent comprising a honey fraction as an active component.

The present invention can be regarded as a honey fraction for use in activating opioid, antitussive, or analgesic. Also, the present invention can be regarded as an agent comprising the honey fraction as an active component for use in activating opioid, antitussive, or analgesic. Further, the present invention can be regarded as use of a honey fraction in the manufacturing of an opioid activator, an antitussive agent, or an analgesic agent.

The above-described embodiment can be regarded as a method of activating opioid, a method of suppressing cough or a method of relieving pain which comprise administering an effective amount of the honey fraction to a subject in need thereof.

Advantageous Effects of Invention

According to the present invention, it is possible to provide a honey fraction having an excellent antitussive action.

DESCRIPTION OF EMBODIMENTS

Figure 1:
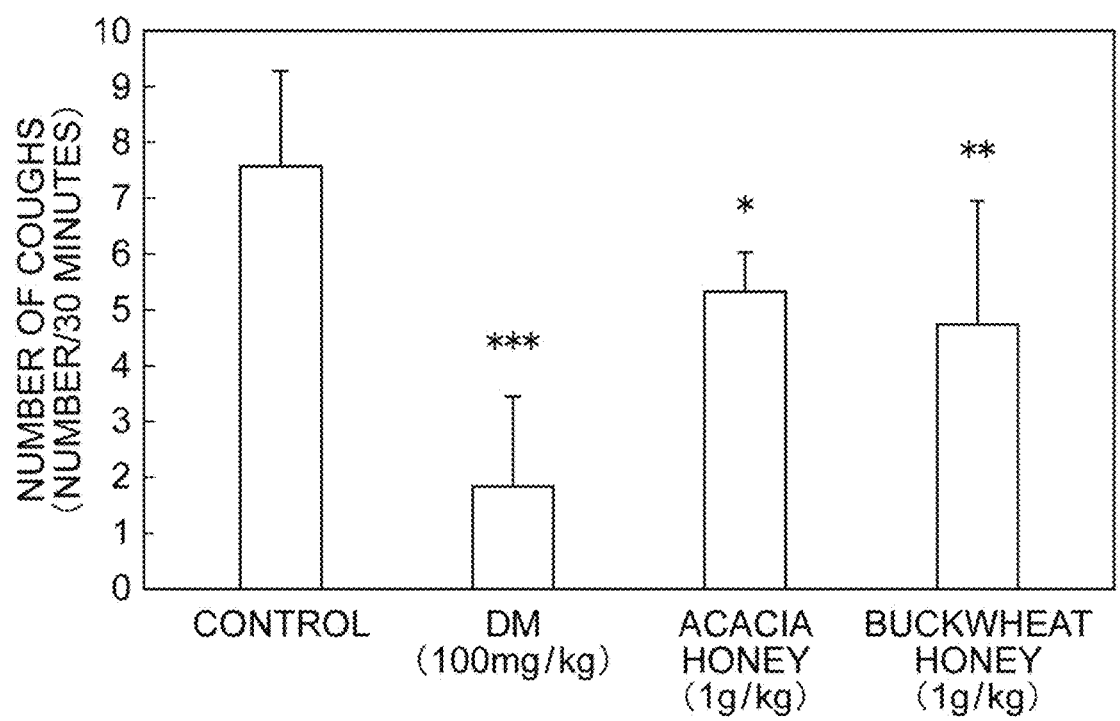
FIG. 1 is a graph illustrating the number of coughs in Test Example 1-1.

Hereinafter, preferred embodiments of the present invention will be described. However, the present invention is not limited to the following embodiments.

The honey fraction according to the present embodiment is obtainable by fractionating honey by a specific method and has high antitussive activity. Specifically, the honey fraction is obtainable by a method comprising (a) causing honey to be brought into contact with an adsorbent so as to obtain an absorbed component which is absorbed to the adsorbent (b) eluting the absorbed component with an organic solvent that is acetone, ethyl acetate, or ethanol so as to obtain an organic solvent fraction, and (c) obtaining a honey fraction from the organic solvent fraction.

The concentration of ethanol used in Step (b) may be 100%, and may be equal to or greater than 99%.

As the adsorbent in Step (a), those commonly used for separating and purifying substances can be used as the adsorbent, and examples thereof include an adsorbent formed of activated carbon, cellulose, silicon dioxide, kaolin, diatomaceous earth, bentonite, silica gel, alumina, zeolite, porous glass, and cyclodextrin, and a synthetic adsorbent. The adsorbent may be porous. Examples of the synthetic adsorbent include an aromatic absorbed component, a dextran derivative absorbed component, and a methacrylic acid ester adsorbent component. As the aromatic absorbed component, a styrene-divinylbenzene adsorbent is preferable. Examples of commercially available styrene-divinylbenzene adsorbent include Diaion HP-20, HP-21, and SP850 (manufactured by Mitsubishi Chemical Corporation), and FPX66, XAD7HP, and FPX62 (manufactured by Organo Corporation). The synthetic adsorbent may be an ionic exchange resin such as an acidic cation exchange resin and a basic anion exchange resin. As the ionic exchange resin, those which are the same as an acid adsorbent and a basic adsorbent described below can be applied. The adsorbent to be used can be packed in a column, for example.

The absorbed component eluted in Step (b) is preferably a component which is not eluted with water or methanol. For example, before Step (b), it is possible to increase the ratio of the component which is not eluted with water or methanol in the absorbed component by eluting the absorbed component obtained in Step (a) with methanol or a methanol aqueous solution, and removing a component that is to be eluted with water, methanol, or a methanol aqueous solution from the absorbed component. As the methanol aqueous solution, a solution having any methanol concentration can be used, for example, a 50% methanol aqueous solution can be used. In addition, for example, it is possible to increase the ratio of the component which is not eluted with water in the absorbed component by dissolving the honey used in Step (a) in water in advance, and causing the obtained solution, as a honey aqueous solution, to be brought into contact with the adsorbent. Through these steps, it is possible to more efficiently obtain a fraction having high antitussive activity.

In addition, the absorbed component eluted in Step (b) may be a component which is not eluted with an ethanol aqueous solution. For example, before Step (b), it is possible to increase the ratio of the component which is not eluted with water or an ethanol aqueous solution from the absorbed component by eluting the absorbed component obtained in Step (a) with an ethanol aqueous solution in advance. The concentration of an ethanol aqueous solution may be, for example, in a range of 20% to 80%, in a range of 40% to 60%, or 50%. Through these steps, it is possible to more efficiently obtain a fraction having high antitussive activity.

Before Step (b), it is preferable to comprise a step of removing a water elutable component from the absorbed component, a step of removing a component which can be eluted with a methanol aqueous solution from the absorbed component, and a step of removing a component which can be eluted with methanol from the absorbed component. These three steps are preferably comprised in this order. With such a fractionation method, it is possible to improve an antitussive action of the obtained honey fraction.

In a case where the obtained honey fraction is used for foods, a solvent for which the absorbed component obtained in Step (a) is eluted in advance is preferably water and ethanol, and the organic solvent in Step (b) is preferably ethanol.

In Step (b), it is preferable that the absorbed component eluted with the organic solvent is further fractionated so as to select a fraction having the higher antitussive activity. The fraction of the absorbed component can be performed by, for example, the elution time when the absorbed component is eluted with the organic solvent.

As a method of selecting a fraction having the high antitussive activity among the fractions, for example, it is possible to use a method of subjecting each fraction to thin layer chromatography using silica gel so as to make the development pattern as an indicator. The absorbed component fractionated by the elution time tends to have a different development pattern of thin layer chromatography depending on its elution time, and depending on the development pattern, it is possible to determine whether or not the absorbed component is an organic solvent fraction including a target honey fraction. A step of fractionating the absorbed component by the elution time so as to obtain the target fraction by using the development pattern of thin layer chromatography as an indicator can be specifically performed by the following Step (b-1) or Step (b-2).

Step (b-1) is a step of obtaining, as the organic solvent fraction, a fraction which has a spot (hereinafter, referred to as a spot A) at a Rf value in a range of 0.49 to 0.55, which is colored with an anisaldehyde sulfuric acid reagent and a spot (hereinafter, referred to as a spot B) at a Rf value in a range of 0.56 to 0.62, which is less colored than the aforementioned spot when the absorbed component eluted with the organic solvent is fractionated by an elution time, and is developed with a solvent in which a mixing ratio of hexane/ethyl acetate is 4/1 in a thin layer chromatography using silica gel.

The fraction having the above-described features has higher antitussive activity. The Rf value of the spot A is preferably in a range of 0.51 to 0.53, and the Rf value of the spot B is preferably in a range of 0.58 to 0.60. As a fraction having a later elution time than that of the honey fraction having high antitussive activity to be desired, a fraction indicating the development pattern in which the spot B has a color development darker than that of the spot A can be obtained.

The anisaldehyde sulfuric acid reagent used in Step (b-1) can be prepared by mixing 13 mL of p-anisaldehyde, 5 mL of acetate, and 478 mL of ethanol with each other, and by adding dropwise 18 mL of concentrated sulfuric acid. In staining with the anisaldehyde sulfuric acid reagent, color development can be confirmed by heating at 105° C. after spraying the reagent.

Step (b-2) is a step of obtaining, as the organic solvent fraction, a fraction which has spots at a Rf value 0, and in a range of 0.54 to 0.94, which are colored with a doragendorf reagent when the absorbed component eluted with the organic solvent is fractionated by the elution time, and is developed with a solvent in which the mixing ratio of chloroform/methanol/acetate is 9/1/1 in the thin layer chromatography using silica gel. The fraction having the above-described features has higher antitussive activity. The Rf value of the spot is preferably 0 and in a range of 0.64 to 0.84, is further preferably 0 and in a range of 0.69 to 0.79, and is still further preferably 0 and in a range of 0.72 to 0.76.

The doragendorf reagent used in Step (b-2) can be prepared by mixing
- 5 mL of mixture prepared by mixing 1.7 g of bismuth subnitrate, 20 mL of acetate, and 80 mL of distilled water,
- 5 mL of admixture prepared by mixing 40 g of potassium iodide, and 100 mL of distilled water,
- 20 mL of acetate, and
- 70 mL of distilled water.

Step (b) may further comprise Step (b-3). Step (b-3) is a step of obtaining, as the organic solvent fraction, a fraction which is detected with a retention time in a range of 2.0 to 4.0 minutes, and has a peak which has molecular ion peaks of m/z 438 [M+H] and m/z 436 [M−H] in a case where the absorbed component eluted with the organic solvent is fractionated by the elution time, and is measured under the following conditions in liquid chromatography mass spectrometry. It is possible to obtain a honey fraction having high antitussive activity by fractionating with such a peak as an indicator. The retention time is preferably in a range of 2.2 to 3.4 minutes, is further preferably in a range of 2.5 to 3.1 minutes, and is still further 2.7 to 2.9 minutes.

The liquid chromatography mass spectrometry can be performed by waters micromass quattro premium (manufactured by Waters Corporation). The measuring conditions of the liquid chromatography mass spectrometry are as follows.

Column: Acquity UPLC BFH C18 ($\varphi$2.1×100 mm, manufactured by Waters Corporation), Flow rate: 0.4 mL/min, Column temperature: 40° C., Solvent: 5% B (0 to 0.25 minutes), 5 to 100% B (0.25 to 10 minutes, linear gradient), 100% B (10 to 12 minutes), 5% B (12 to 15 minutes), A: 0.05% of formic acid aqueous solution, B: 100% of acetonitrile, Detection wavelength: 295.8 nm, Detection mass: SIR mode: positive mode m/z (cone): 93.2 (10), 239.1 (10), 255.4 (30), 257.1 (30), 438.5 (30), 585.3 (30), negative mode m/z (cone): 112.9 (30), 175.0 (30), 253.2 (30), 255.2 (30), 285.6 (30), 449.8 (30), 577.8 (30), Injection volume: 2 μl Step (b-1), Step (b-2), and Step (b-3) may be performed alone, or may be in combination. When performing Step (b-2) or Step (b-3), it is possible to obtain a honey fraction having the high antitussive activity as compared with a case where only Step (b-1) is performed.

Step (b-4)

In Step (b), it is preferable that the fraction obtained in Step (b-2) is further fractionated so as to select a fraction having the higher antitussive activity. Further fractionation of the fraction obtained in Step (b-2) can be performed by, for example, subjecting the fraction obtained in Step (b-2) to reverse phase chromatography using a reverse phase adsorbent. As a method for selecting the fraction having the higher antitussive activity from the obtained fraction, for example, a method of subjecting each fraction to thin layer chromatography using silica gel so as to make the development pattern as an indicator can be used. The fraction which is fractionated by the elution time of the reverse phase chromatography tends to have a different development pattern of thin layer chromatography depending on its elution time, and depending on the development pattern, it is possible to determine whether or not the fraction includes a target honey fraction. Specifically, the above method can be performed in the following Step (b-4).

Step (b-4) is a step of obtaining the fraction satisfying at least one of the conditions of the following (1) and (2) as an organic solvent fraction by further fractionating the fraction obtained in Step (b-2) with a reverse phase adsorbent.
(1) Having a spot at a Rf value in a range of 0 to 0.22 which is colored with a doragendorf reagent when the development is performed with a solvent in which the mixing ratio of chloroform/methanol/acetate is 9/1/0.3 in the thin layer chromatography using silica gel
(2) Having at least one spot selected from the group consisting of the spots at Rf values in a range from 0.02 to 0.09, 0.10 to 0.20, and 0.30 to 0.53, which is colored with a ninhydrin reagent when the development is performed with a solvent in which the mixing ratio of chloroform/methanol/water is 1/1/0.3 in the thin layer chromatography using silica gel The ninhydrin reagent can be prepared by mixing, for example, 0.3 g of ninhydrin, 3 mL of acetate, and 100 mL of n-butanol. In staining with the ninhydrin reagent, color development can be confirmed by heating at 105° C. after spraying the reagent.

The reverse phase chromatography can be performed by high performance liquid chromatography using a reverse column such as an ODS (C18) column, a C8 column, and a C30 column. Examples of commercially available reverse phase ODS column include cosmosil 5c-18-AR-II (manufactured by NACALAI TESQUE); Capcell Pak C18 AQ (manufactured by Shiseido Company, Limited); Sunfire C18 and Atlantis T3 (manufactured by Waters Corporation); inertsill ODS-3 (manufactured by GL Sciences Inc.) and TSK gel ODS-100S (manufactured by TOSOH CORPORATION); Cadenza CD-C18 (manufactured by Imtakt Corp.), Hydrosphere C18, Pro C8, and Pro C18 (manufactured by YMC. Co., Ltd.); and Develosil HB ODS-U G-3, Develosil HB ODS-H G-3, and Develosil HB C30-U G-3 (manufactured by DEVELOSIL).

Regarding the spot of the thin layer chromatography development pattern in the above (1), the Rf value is preferably in a range of 0 to 0.12, and the Rf value is further preferably in a range of 0 to 0.06. The thin layer chromatography development pattern in the above (2) preferably has at least one spot selected from the group consisting of the spots at the Rf values in a range of 0.04 to 0.07, 0.10 to 0.18, and 0.30 to 0.53, and further preferably has the Rf value in a range of 0.10 to 0.18.

In Step (c), a honey fraction is obtained from the organic solvent fraction obtained in Step (b). The honey fraction can be obtained by removing the solvent in the organic solvent fraction, for example. The removing of the solvent can be performed by, for example, freeze drying, heat drying, and the like.

The honey fraction according to the present embodiment can be obtained by a method including (d) a step of causing honey to be brought into contact with an acid adsorbent so as to obtain an absorbed component which is absorbed to the acid adsorbent (e) a step of obtaining a basic aqueous solution fraction by eluting the absorbed component with the basic aqueous solution, and (f) a step of obtaining a honey fraction from the basic aqueous solution fraction. The honey fraction that can be obtained by the above-described method has the high antitussive activity.

Specifically, Step (d) can be performed by, for example, allowing a honey aqueous solution dissolved in water such as ion exchanged water to flow into the acid adsorbent such as an acidic cation exchange resin. The ionic form of the acidic cation exchange resin may be, for example, a salt form such as calcium ion form, sodium ion form or the like. The acidic cation exchange resin may be a strongly acidic cation exchange resin or a weakly acidic cation exchange resin. Examples of the acidic cation exchange resin include AMBERLITE 200CTNA (manufactured by Organo Corporation); and SK1B, SK104, SK110, SK112, PK208, PK212, PK216, PK218, PK220, PK228, UBK530, UBK535, UBK530K, UBK535K, UBK555, WK40, WK10, WK11, and WK100 (which are all manufactured by Mitsubishi Chemical Corporation). The acidic cation exchange resin is preferably conditioned beforehand with an acidic aqueous solution and water. As the acidic aqueous solution used for the conditioning, 1 M hydrochloric acid is preferably used, for example.

As the basic aqueous solution used in Step (e), an aqueous solution of pH 8 to 9 such as ammonia water can be used for example. The basic aqueous solution may contain ethanol. The absorbed component eluted in Step (e) is preferably a component which is not eluted with water. For example, before Step (e), when the absorbed component obtained in Step (d) is eluted with water, and the component which is eluted with water from the absorbed component is removed, an absorbed component eluted in the next Step (e) can be a component which is not eluted with water.

In Step (f), the honey fraction can be obtained by removing the solvent in the basic aqueous solution fraction, for example. The removing of the solvent can be performed by, for example, freeze drying, heat drying, and the like.

The honey fraction according to the present embodiment can be obtained by a method including (d') a step of causing honey to be brought into contact with a basic adsorbent so as to obtain an absorbed component which is absorbed to the basic adsorbent, (e') a step of obtaining an acidic aqueous solution fraction by eluting the absorbed component with the acidic aqueous solution, and (f') a step of obtaining a honey fraction from the acidic aqueous solution.

Specifically, Step (d') can be performed by, for example, allowing a honey aqueous solution dissolved in water such as ion exchanged water to flow into the basic adsorbent such as a basic anion exchange resin. The ionic form of the basic anion exchange resin may be, for example, a chloride ion type. The basic anion exchange resin may be a strongly basic anion exchange resin or a weakly basic anion exchange resin. The basic anion exchange resin is preferably a MR type, and is preferably a styrene type. Examples of the basic anion exchange resin include AMBERLITE 2 IRA910CT, IRA402BL (manufactured by Organo Corporation), SA10A, SA12A, SA11A, NSA100, and UBA120 (uniform grain size article), PA306S, PA308, PA312, PA316, PA318L, HPA25, SA20A, SA21A, PA408, PA412, PA418, WA10, WA20, WA21J, and WA30 (manufactured by Mitsubishi Chemical Corporation). The basic anion exchange resin is preferably conditioned beforehand with a basic aqueous solution and water. As a basic aqueous solution used for conditioning, 1 M sodium hydroxide aqueous solution or the like is preferable, for example.

The honey aqueous solution is preferably adjusted to basic (pH 8 to 9). The pH can be adjusted by adding a basic aqueous solution such as ammonia water to the honey aqueous solution.

As the acidic aqueous solution used in Step (e'), for example, an aqueous solution having a pH of 2 to 3 of a hydrochloric acid, a phosphoric acid, acetate, a citric acid or the like can be used. The acidic aqueous solution may contain ethanol. The absorbed component eluted in Step (e') is preferably a component which is not eluted with water. For example, before Step (e'), when the absorbed component obtained in Step (d') is eluted with water, and the component which can be eluted with water from the absorbed component is removed, an absorbed component eluted in the next Step (e') can be a component which is not eluted with water.

In Step (f'), the honey fraction can be obtained by removing the solvent in the basic aqueous solution fraction, for example. The removing of the solvent can be performed by, for example, freeze drying, heat drying, and the like.

In Step (d), before causing honey to be brought into contact with acid adsorbent, the honey may be fractionated in advance by performing the same step as Steps (d') and (e') as described-above. That is, in Step (d), an absorbed component which is absorbed to an acid adsorbent may be obtained by performing the step of causing honey to be brought into contact with a basic adsorbent so as to obtain an absorbed component which is absorbed to the basic adsorbent, and the step of obtaining an acidic aqueous solution fraction by eluting the absorbed component with an acidic aqueous solution, followed by causing the acidic aqueous solution fraction to be brought into an acid adsorbent.

In contrast, in the above-described Step (d'), before causing honey to be brought into the basic adsorbent, the honey may be fractionated in advance by performing the same step as Steps (d) and (e) as described-above. That is, in Step (d'), an absorbed component which is absorbed to a basic adsorbent may be obtained by performing the step of causing honey to be brought into contact with an acid adsorbent so as to obtain an absorbed component which is absorbed to the acid adsorbent, and the step of obtaining a basic aqueous solution fraction by eluting the absorbed component with the basic aqueous solution, followed by causing the basic aqueous solution fraction to be brought into an basic adsorbent.

In this way, through the steps of causing honey to be brought into contact with the different kinds of adsorbents, it is possible to obtain a honey fraction having higher antitussive activity.

The origin of honey used in this embodiment is not particularly limited, and any kind of honey can be used. As honey, for example, polyfloral honey, acacia honey, buckwheat honey, honeydew honey and the like can be mentioned. A production area of honey is not particularly limited.

The honey fraction according to the present embodiment has the high antitussive activity. Specifically, by consuming the honey fraction according to the present embodiment, cough can be prevented or suppressed. Accordingly, the honey fraction can be used as an antitussive agent, and the antitussive agent can be used as a cough preventive or a cough suppressant.

The above-described embodiment can also be regarded as a honey fraction for use in antitussive. The embodiment can also be regarded as an agent comprising a honey fraction as an active component for use in antitussive. The embodiment can also be regarded as use of the honey fraction in the manufacturing of the antitussive agent.

The above-described embodiment can be regarded as a method of suppressing cough comprising administering an effective amount of the honey fraction to a subject in need thereof. A dosage can be appropriately set depending on the fractionation method of the honey fraction, and for example, it can be in a range from 0.01 mg to 100 g per day for adults weighing 60 kg. The subject is preferably a mammal, and is further preferably a human.

The cough is induced by stimulation of a cough receptor. It is considered that there are a rapidly adapting receptor (RARs) existing in Aδ-fiber and a C-fiber receptor as the cough receptor. The honey fraction according to the present embodiment has an antitussive action for any kind of cough caused by various factors, as described in the examples below.

The honey fraction according to the present embodiment has opioid activity. Specifically, at least a part of the physiological action of the honey fraction according to the present embodiment is due to an action exerted mediated by the opioid receptor (opioid activity) as described in Examples described below. Therefore, the honey fraction according to the present embodiment can be used as an opioid activator.

The above-described embodiment described above can also be regarded as a honey fraction for use in activating opioid. The embodiment can also be regarded as an agent comprising the honey fraction as an active component for use in activating opioid. The embodiment can also be regarded as use of the honey fraction in the manufacturing of the opioid activator.

The above-described embodiment can be regarded as an opioid activating method which comprises administering an effective amount of the honey fraction to a subject in need thereof. A dosage can be appropriately set depending on the fractionation method of the honey fraction, and for example, it can be in a range from 0.001 mg to 100 g per day for adults weighing 60 kg. The subject is preferably a mammal, and is further preferably a human.

It has been known that in addition to the antitussive activity, the opioid activity is related to analgesia, anesthesia, emotion, breathing, pulsation, a body temperature, a gastrointestinal function, food intake, immunity, regulation of hormone secretion such as insulin and somatostatin, promotion of absorption of electrolyte, and regulation of myocardium contraction (References: Shigeki Yamaguchi, "Mechanism of action of opioid analgesics", Anet, Vol. 18, No. 3, Pages 12-15, 2014, JP h06-128287 A). Accordingly, the opioid activator comprising the honey fraction according to the present embodiment as an active component can be used as, for example, an antitussive agent, an analgesic agent, an anesthetic agent, an emotion regulating agent, a respiratory regulating agent, a pulsation regulating agent, a body temperature regulating agent, a gastrointestinal function regulating agent, a food intake regulating agent, an immunity improver, a hormone secretion regulating agent, an electrolyte absorption promoting agent, and a myocardial contraction regulating agent. The honey fraction according to the present embodiment is particularly preferably used as an antitussive agent or an analgesic agent.

The opioid activator, the antitussive agent, analgesic agent, and other agents according to the embodiment may comprise only the honey fraction which is an active component, and may comprise a solvent and other components as long as the physiological actions such as an antitussive effect and an analgesic effect are not prevented. Examples of other components include pharmaceutically acceptable additives (an excipient, a binder, a lubricant, a disintegrant, an emulsifier, a surfactant, a base, a solubilizer, and a suspending agent), acceptable ingredients for the foods (for example, minerals, vitamins, flavonoids, quinones, polyphenols, an amino acid, a nucleic acid, an essential fatty acid, a cooling agent, a binder, a sweetener, a disintegrant, a lubricant, a colorant, a fragrance, a stabilizer, a preservative, a sustained release control agent, a surfactant, a dissolving agent, and a wetting agent).

The ratio of the honey fraction comprised in the opioid activator, the antitussive agent, the analgesic agent, and other agents according to the present embodiment may be within the range where the effect of the present invention can be obtained, and it is appropriately adjusted depending on the final form, for example, is in a range from 0.000001 to 100% by mass in a total amount.

The honey fraction, the opioid activator, the antitussive agent, the analgesic agent, and other agent according to the present embodiment may be in any form of solid, liquid, paste, and the like, or may be a dosage form such as a tablet (including an uncoated tablet, a sugar-coated tablet, an effervescent tablet, a film-coated tablet, a chewable tablet, and a lozenge, and the like), a capsule, a pill, powder (powder medicine), fine granule, granule, liquid, suspension, emulsion, syrup, paste, and injection (including the case where it is prepared as a liquid formulation by mixing it with distilled water or an infusion solution such as amino acid infusion or electrolyte infusion at the time of use). These various preparations can be prepared, for example, by mixing honey fraction, which is an active component, and other components as required, and forming into the above dosage form.

The honey fraction according to the present embodiment can be used as the pharmaceuticals and foods themselves, and can be used by being added to the pharmaceuticals and foods. As the foods, foods having third-order functions of the foods, that is, foods in which a physical adjusting function is enhanced are preferable. Examples of the physical adjusting function include an antitussive function, an analgesic function, an anesthetic function, an emotion regulating function, a respiratory regulating function, a pulsation regulating function, a body temperature regulating function, a gastrointestinal function regulating function, an food intake regulating function, an immunity improving function, a hormone secretion regulating function, an absorption promoting function of electrolyte, and a myocardial contraction regulating function. Examples of the foods in which the third-order functions are emphasized include health foods, functional foods, nutritional supplementary foods, supplement, and foods for specified health use.

The pharmaceuticals or foods consisting of the honey fraction according to the present embodiment, or the pharmaceuticals or foods comprising the honey fraction according to the present embodiment may be used as pharmaceuticals or foods for antitussive, analgesic, anesthetic, emotion regulation, respiratory regulation, pulsation regulation, temperature regulation, gastrointestinal function regulation, food intake regulation, immunity improvement, hormone secretion regulation, promotion of electrolyte absorption, and regulation of myocardial contraction. Further, indications that representing the effects of quelling cough, of relieving pain, of having an anesthetic action, of regulating emotion, of regulating respiratory, of regulating pulsation, of regulating a body temperature, of regulating a gastrointestinal function, of regulating food intake, of improving immunity, of regulating hormone secretion, of promoting absorption of electrolyte, and of regulating myocardial contraction may be attached to the pharmaceuticals or the foods.

In a case of using the honey fraction according to the present embodiment by being added to the foods (for example, health foods, functional foods, nutritional supplementary foods, and foods for specified health use), the form of the foods is not particularly limited, and examples thereof include beverages (soft drinks such as coffee, juice, and tea drinks, milk drinks, lactobacillus drinks, yogurt drinks, and carbonated beverages); spreads (such as custard cream); paste (such as fruit paste); confectionery (such as chocolate, donut, pie, cream puff, gum, jelly, candy, cookie, cake, and pudding); Japanese sweets (such as Daifuku, rice cake, sweet bun, Castella, Anmitsu, and sweet beans jelly); frozen desserts (ice cream, ice candy, and sorbet); foods (curry, beef bowl, rice cooker, miso soup, soup, meat sauce, pasta, pickles, and jam); and seasonings (dressing, sprinkle, umami seasoning, and soup ingredients).

The manufacturing method of the pharmaceuticals or the foods to which the honey fraction according to the embodiment is added is not particularly limited, and can be appropriately followed a known method. For example, it is possible to obtain the pharmaceuticals or the foods used for the above applications by mixing the honey fraction according to the present embodiment to an intermediate product or a final product in steps of manufacturing the pharmaceuticals or the foods.

EXAMPLES

Hereinafter, the embodiments of the present invention will be specifically described with reference to examples. The present invention is not limited to the following examples.

Test Example 1

The effects of various kinds of honey on a guinea pig having a cough induced by various stimulation were examined.

Test Example 1-1

Stimulation with Citric Acid

In order to confirm an action on cough mediated by rapidly adapting receptor (RARs) existing in Aδ-fiber, an antitussive action of the honey on the cough induced by a citric acid stimulating the RARs was examined.

Acacia honey from Romania or buckwheat honey from Japan was administered intragastrically to normal a guinea pig at a ratio of 1 g of honey per 1 kg of body weight of the guinea pig (hereinafter, referred to as 1 g/kg). As the intragastrically administered honey, the honey dissolved in water was used. In 30 minutes after administration, a citric acid (0.1 M) was sprayed for 5 minutes, and the number of cough reflexes was counted for 30 minutes immediately after the start of spraying. As a control, the cough was induced by the citric acid and the number of cough reflexes was measured in the same method as above except that water or a dextromethorphan (DM) aqueous solution (DM 100 mg/kg) was used instead of the honey aqueous solution. The results are illustrated in FIG. 1. With 1 g/kg of administration of the acacia honey or the buckwheat honey, the number of coughs is significantly reduced as compared with a case where only water was given.

Test Example 1-2

Stimulation with Capsaicin

Figure 2:
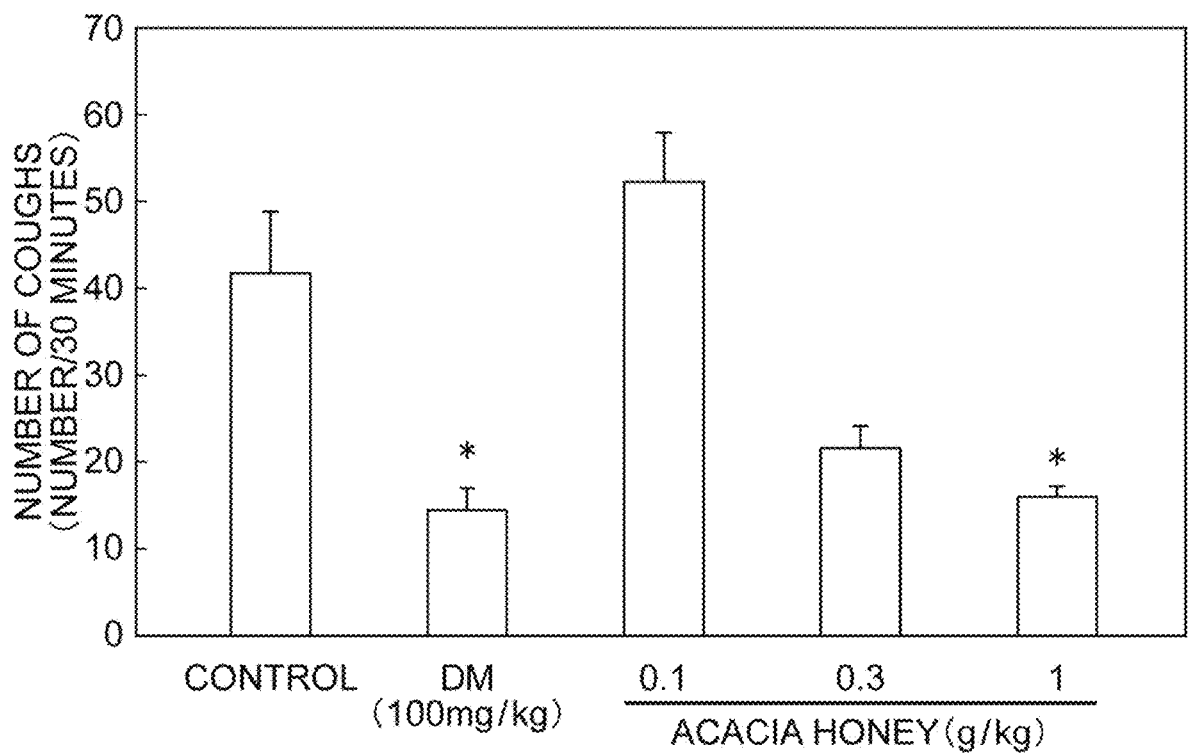
FIG. 2 is a graph illustrating the number of coughs in Test Example 1-2.

An antitussive action of the honey was examined by using capsaicin which induces cough mediated by C-fiber. An acacia honey aqueous solution was intragastrically administered to normal a guinea pig at a rate of 0.1 g/kg, 0.3 g/kg, or 1 g/kg of honey. In 30 minutes after administration, capsaicin ($10^{-5}$M) was sprayed for 5 minutes, and the number of cough reflexes was counted for 30 minutes. As the control, water or a DM aqueous solution (100 mg/kg) was used instead of the honey aqueous solution. The results are illustrated in FIG. 2. With 1 g/kg of administration of the acacia honey, an antitussive effect which is almost equivalent to DM (100 mg/kg) was exhibited. In addition, it is indicated that the antitussive action of the honey is concentration-dependent.

Test Example 1-3

Stimulation with Tobacco Smoke

Figure 3:
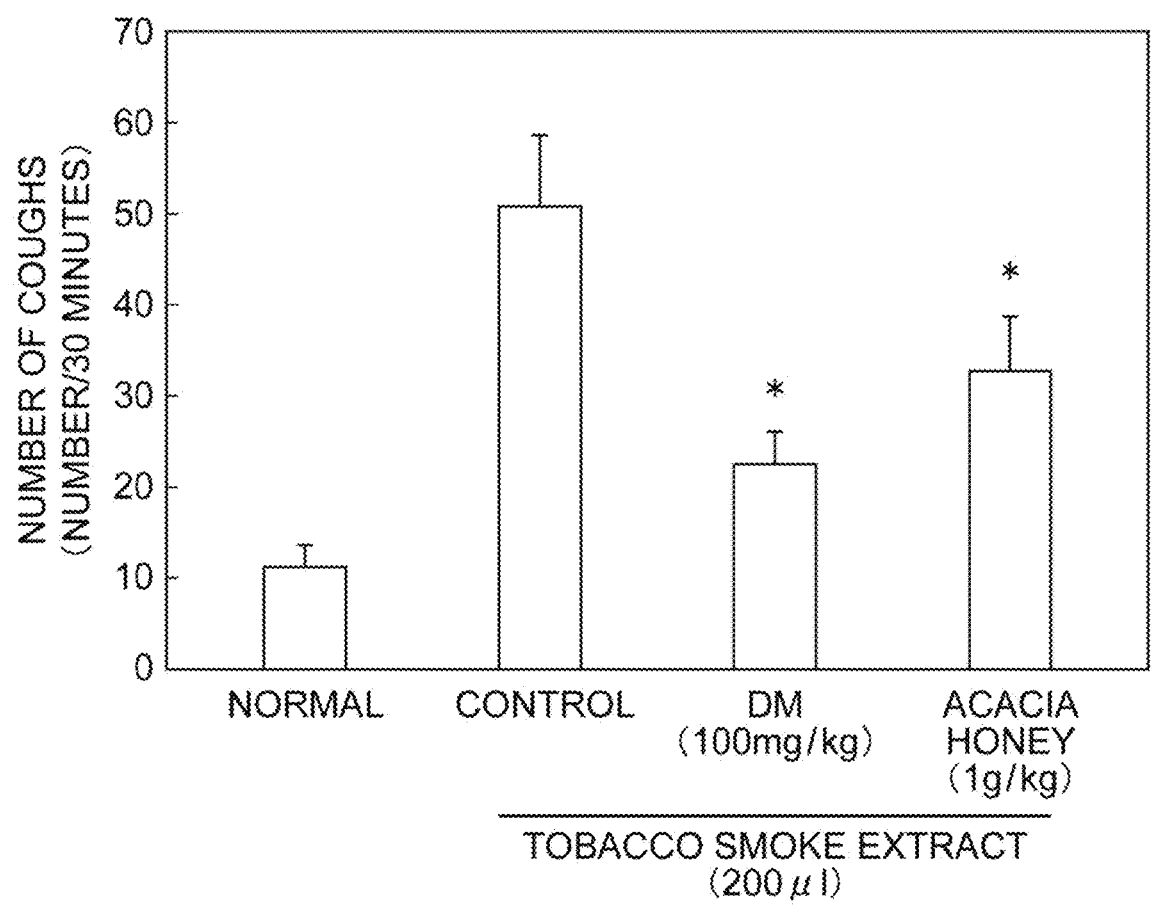
FIG. 3 is a graph illustrating the number of coughs in Test Example 1-3.

The antitussive action of the honey was examined by causing the guinea pig to be induced by stimulation with a citric acid by using the same method as that used in Test Example 1-1 except that the guinea pig having airway inflammation induced by administering a tobacco smoke extract (CSE) into a trachea of the guinea pig for one week was used, and only the acacia honey was used as honey. The results are illustrated in FIG. 3. The number of coughs of a healthy guinea pig without CSE administration is also shown. With 1 g/kg of administration of the acacia honey, an antitussive effect which is almost equivalent to DM (100 mg/kg) was exhibited.

Test Example 1-4

Stimulation with Sulfur Dioxide Gas

Figure 4:
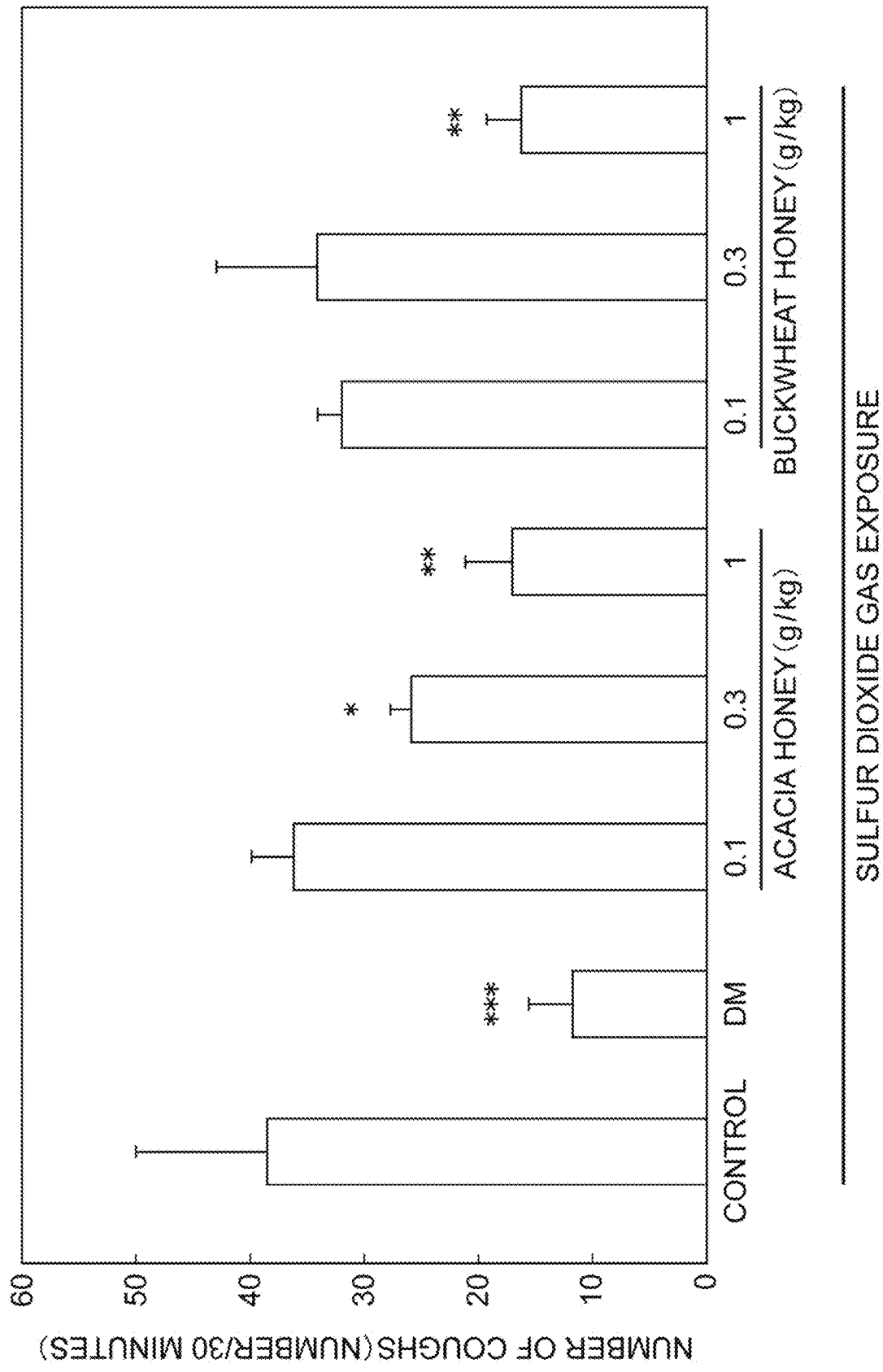
FIG. 4 is a graph illustrating the number of coughs in Test Example 1-4.

An action of honey on the cough induced by the stimulation with citric acid was examined by using a sulfur dioxide gas-exposed guinea pig which is known to exhibit characteristic pathology of subacute orbital inflammation such as increased mucus retention, increased sensitivity, and neutrophil wetness. The antitussive action of the honey was examined by causing the guinea pig to be induced by stimulation with a citric acid with the same method as that used in Test Example 1-1 except that a guinea pig exposed to a sulfur dioxide gas for 1 week was used, and the honey administration rate was set to 0.1 g/kg, 0.3 g/kg, or 1 g/kg. The results are illustrated in FIG. 4. With 1 g/kg of administration of the acacia honey and the buckwheat honey, an antitussive effect which is almost equivalent to DM (100 mg/kg) was exhibited.

Test Example 1-5

Ovalbumin

Figure 5:
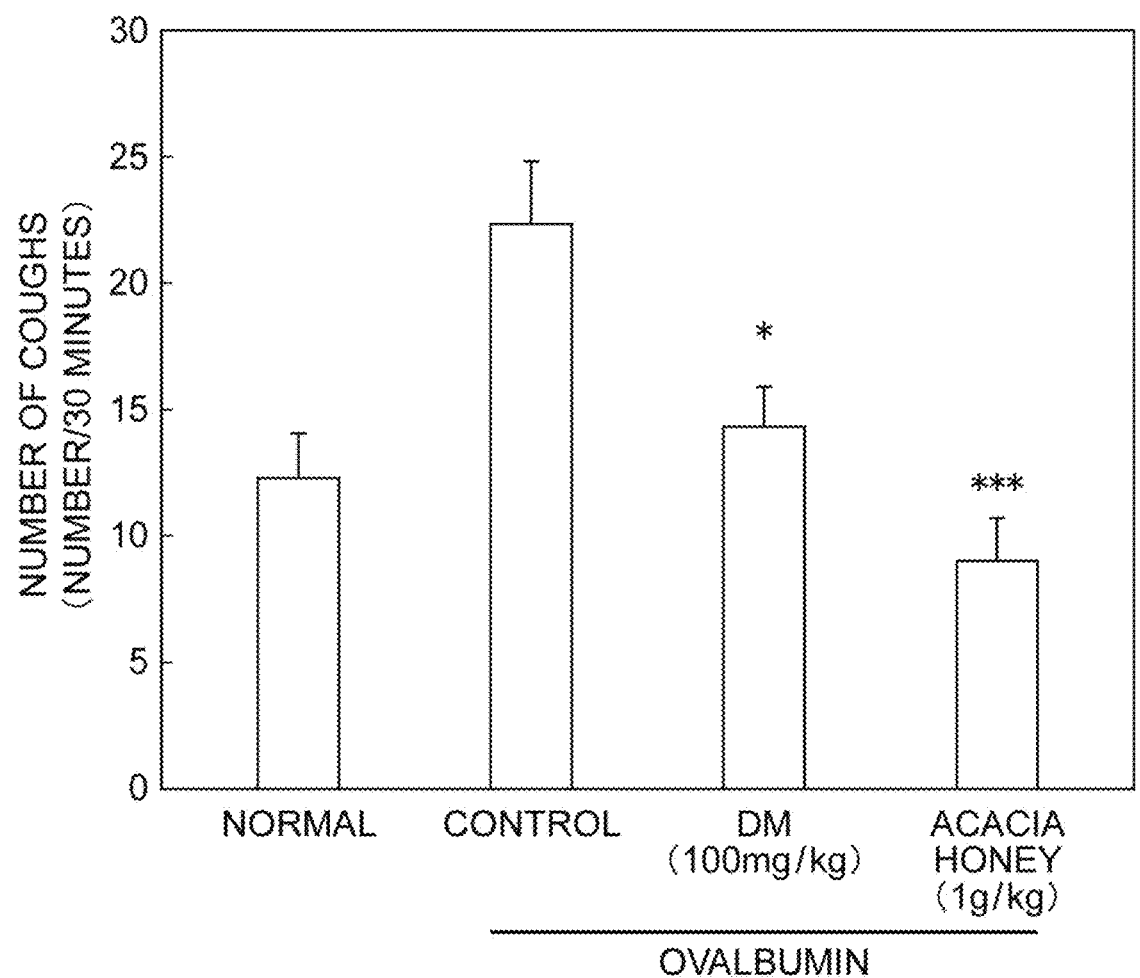
FIG. 5 is a graph illustrating the number of coughs in Test Example 1-5.

In order to confirm an action on cough in eosinophilic inflammation typified by cough asthma, atopic cough, or the like, the antitussive action of the honey was examined by preparing a bronchial asthma model due to ovalbumin (OVA) sensitization, and by causing the guinea pig to be induced by stimulation with a citric acid by using the same method as that used in Test Example 1-1. As the bronchial asthma model, only an individual in which the OVA was subcutaneously administered to the left auricle, and is positive for an anaphylactic reaction was used for the test. The results are illustrated in FIG. 5. With 1 g/kg of administration of the acacia honey, an antitussive effect was shown which was higher than DM (100 mg/kg).

Test Example 1-6

Figure 6:
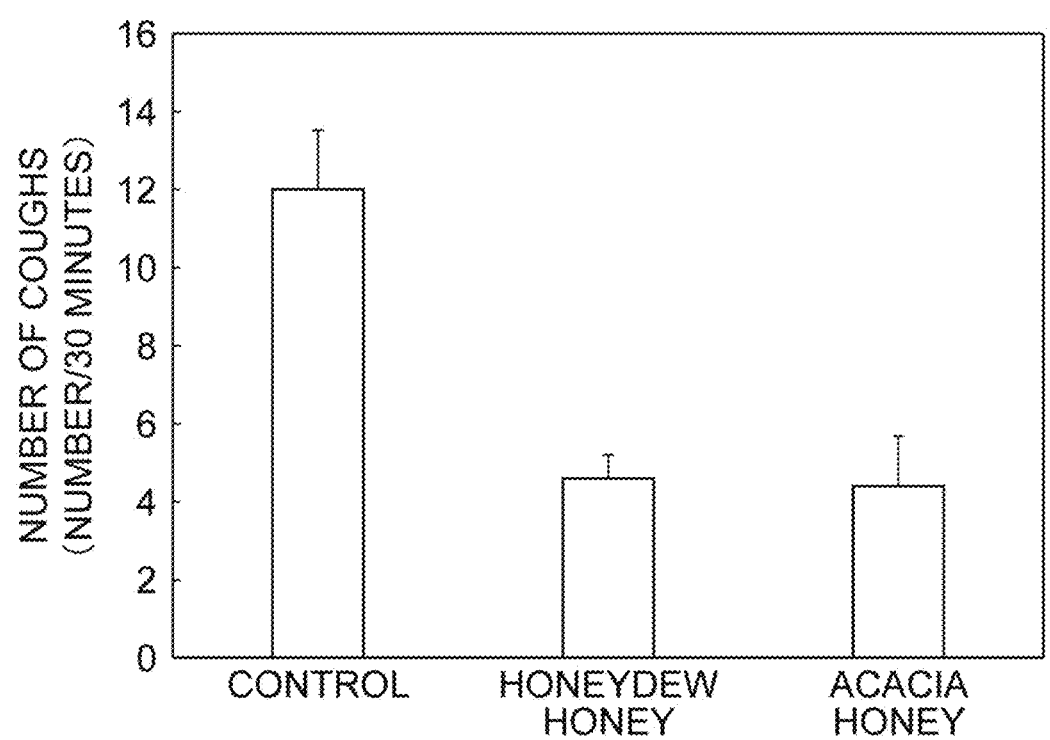
FIG. 6 is a graph illustrating the number of coughs in Test Example 1-6.

Each of the honeydew honey (0.8 g/kg) and the acacia honey (1 g/kg) was intragastrically administered to the normal guinea pig. As the intragastrically administered honey, the honey dissolved in water was used. Similar to the above-described Test Example 1-1, in 30 minutes after administration, a citric acid (0.1 M) was sprayed for 5 minutes, and the number of cough reflexes was counted for 30 minutes immediately after the start of spraying. As the control, water was used instead of the honey aqueous solution. The results are illustrated in FIG. 6. It was confirmed that the honeydew honey has the same antitussive activity as that of the acacia honey.

Test Example 2

Test Example 2-1

100.00 g of acacia honey was weighed and dissolved in 2 L of water to prepare a honey aqueous solution. The honey aqueous solution was allowed to slowly flow 5 times into a column (φ5×31 cm, 500 mL) packed with Diaion HP-20 (manufactured by Mitsubishi Chemical Corporation), and the unabsorbed components were collected as a water fraction. A 50% methanol aqueous solution, methanol, and acetone were allowed to sequentially flow, for 2 L each, into the above column, and were collected as a 50% methanol fraction (16.86 g), a methanol fraction (98.33 mg), and an acetone fraction (52.03 mg) (the inside of the parenthesis indicates the amount of honey fraction excluding the solvent in each fraction. Hereinafter, the same applies). The water fraction was freeze dried and the weight thereof was measured. As a result, the amount of honey fraction excluding water in the water fraction was 73.1 g.

Figure 7:
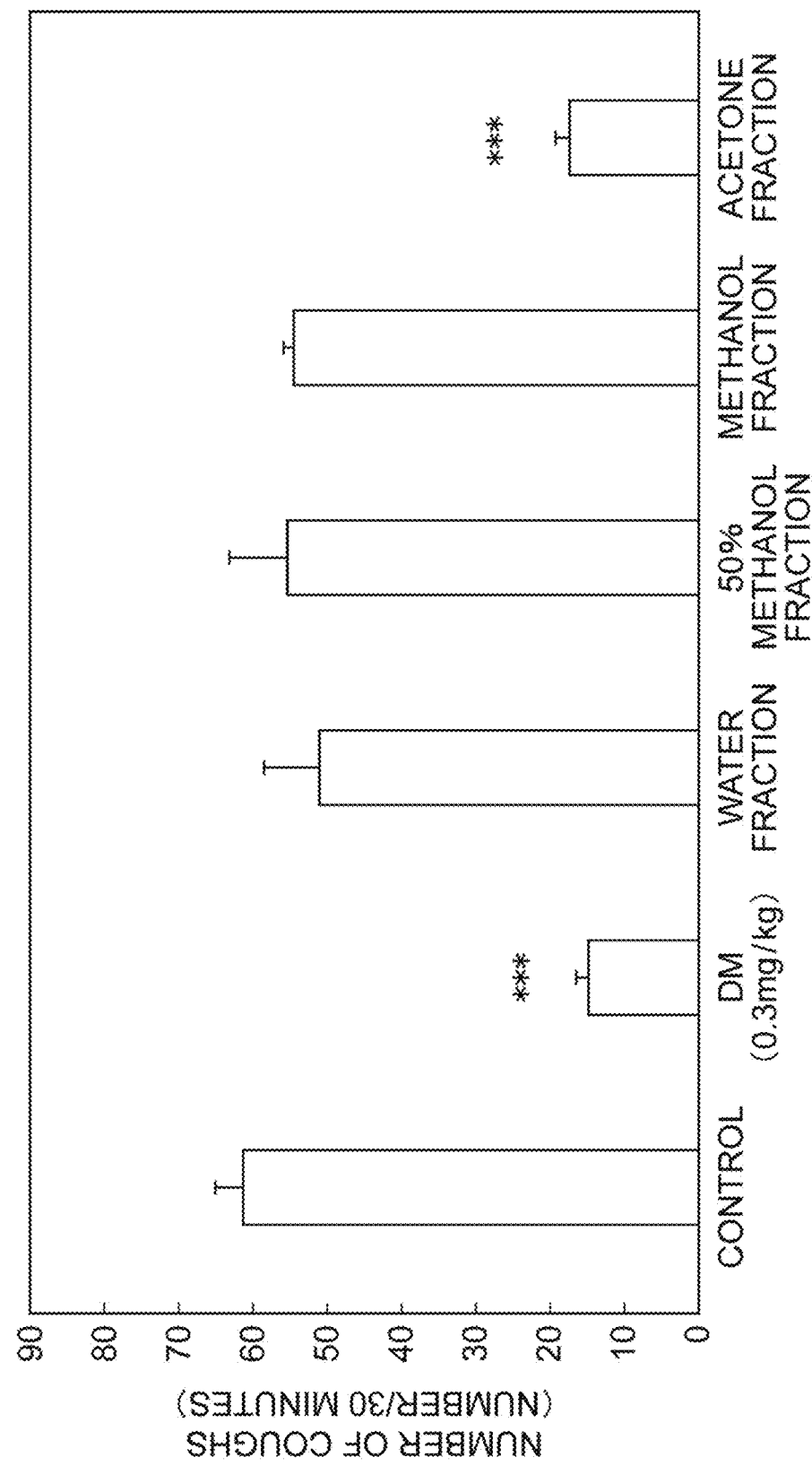
FIG. 7 is a graph illustrating the number of coughs in Test Example 2-1.

An amount equivalent to 1 g/kg of honey of each honey fraction dissolved in water was intragastrically administered to the normal guinea pig. In 30 minutes after administration, a citric acid (0.1 M) was sprayed for 5 minutes, and the number of cough reflexes was counted for 30 minutes immediately after the start of spraying. As the control, water or a DM aqueous solution (DM 0.3 mg/kg) was used instead of the honey aqueous solution. The results are indicates in FIG. 7 (average±standard deviation, n=5 to 6, ***: p<0.0001 (with respect to the control)). It was confirmed that 0.52 mg/kg of acetone fraction has a clear antitussive effect which is comparable to 0.3 mg/kg of DM. As compared with the honey before the fraction, the specific activity of the honey fraction in the acetone fraction was 1,923 times.

Test Example 2-2

200.00 g of acacia honey was weighed and dissolved in 4 L of water to prepare a honey aqueous solution. The honey aqueous solution was allowed to slowly flow 5 times into a column (φ5×31 cm, 500 mL) packed with Diaion HP-20, then, a 50% methanol aqueous solution and methanol were allowed to sequentially flow, for 4 L each, into the above column, and the solvent were collected as a 50% methanol fraction (30.54 g) and a methanol fraction (41.56 mg). Further, 4 L of acetone was allowed to flow into the above column, and the acetone fraction was fractionated every elution time.

Figure 8:
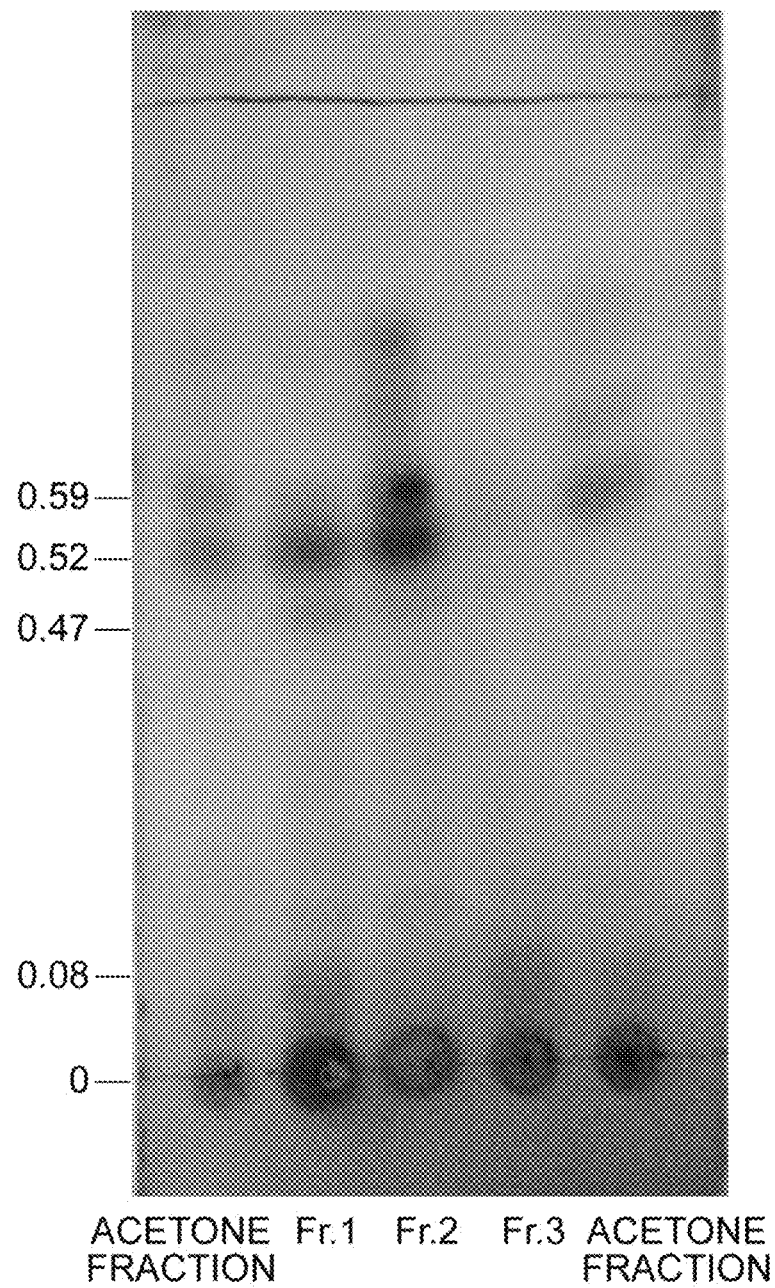
FIG. 8 is a diagram illustrating a thin layer chromatography pattern in Test Example 2-2.

The honey fraction obtained in the acetone fractions was subjected to thin layer chromatographic analysis. 10 mg of each sample dissolved in 1 mL of acetone was spotted by using Silica Gel 60F254 plate (0.5 mm). The development was performed with a solvent in which a mixing ratio of hexane/ethyl acetate is 4:1, and after drying, an anisaldehyde sulfuric acid test solution was sprayed on the plate and heated at 105° C. so as to develop the color. As the anisaldehyde sulfuric acid reagent, a solution in which 13 mL of p-anisaldehyde, 5 mL of acetate, and 478 mL of ethanol were mixed with each other, and 18 mL of concentrated sulfuric acid was added dropwise was used. Development patterns of the honey fraction was classified into three kinds, and each of them was set as an acetone fraction 1 (27.8 mg), an acetone fraction 2 (51.4 mg), and an acetone fraction 3 (9.89 mg) in order of the elution time. The development results of the entire acetone fractions and the acetone fractions 1 to 3 are illustrated in FIG. 8. The acetone fraction 1 had at least a spot at a Rf value of 0.08, 0.47, 0.52, and 0.59, and had a feature that a spot at the Rf value of 0.59 is less colored than a spot at a Rf value of 0.52. The acetone fraction 2 had at least a spot at the Rf value of 0.52 and 0.59, and had a feature that a spot at the Rf value of 0.59 is the most darkly colored. The acetone fraction 3 had a feature that a whole lane is lightly colored.

Figure 9:
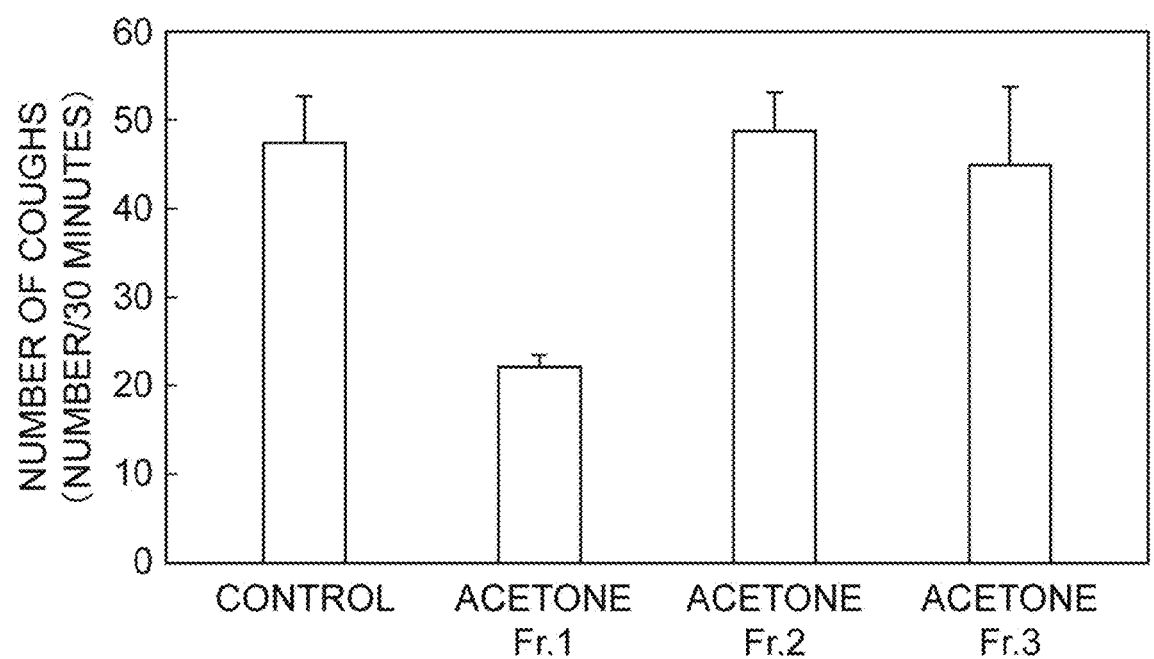
FIG. 9 is a graph illustrating the number of coughs in Test Example 2-2.

Regarding the acetone fractions 1 to 3, the honey fraction obtained by removing a solvent from each of the fractions was dissolved in water, and an amount equivalent to 1 g/kg of honey in each fraction was intragastrically administered to the normal guinea pig. In 30 minutes after administration, a citric acid (0.1 M) was sprayed for 5 minutes, and the number of cough reflexes was counted for 30 minutes immediately after the start of spraying. As the control, water was used instead of the honey fraction aqueous solution. The results are illustrated in FIG. 9. The high antitussive activity was found in the acetone fraction 1 (0.14 mg/kg). As compared with the honey before the fraction, the specific activity of the honey fraction in the acetone fraction 1 was 7,143 times.

Regarding the methanol fraction and the acetone fractions 1 and 2, analysis was performed by waters micromass quattro premium (LCMS (manufactured by Waters Corporation)) under the following conditions. As a column, Acquity UPLC BFH C18 (φ2.1×100 mm, manufactured by Waters Corporation) was used. A mobile phase was set as a 0.05% formic acid aqueous solution (A) and 100% acetonitrile (B), and a gradient was set as 5% B (0 to 0.25 minutes), 5 to 100% B (0.25 to 10 minutes, a linear gradient), 100% B (10 to 12 minutes), and 5% B (12 to 15 minutes). Detection was performed under the conditions that an injection volume was set to 2 µl, a flow rate was set to 0.4 mL/min, a column temperature was set to 40° C., and UV was set to 295.8 nm. In addition, a molecular ion peak was detected under the following conditions.

MS detection method: SIR
Mode: Positive mode m/z (cone): 93.2 (10), 239.1 (10), 255.4 (30), 257.1 (30), 438.5 (30), 585.3 (30), negative mode m/z (cone): 112.9 (30), 175.0 (30), 253.2 (30), 255.2 (30), 285.6 (30), 449.8 (30), 577.8 (30)

Figure 10:
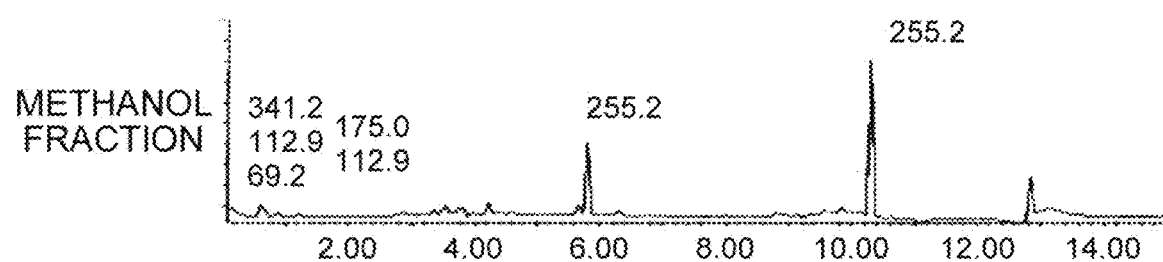
FIGS. 10(a), (b), and (c) are diagrams illustrating a LCMS chart in Test Example 2-2.
Figure 10:
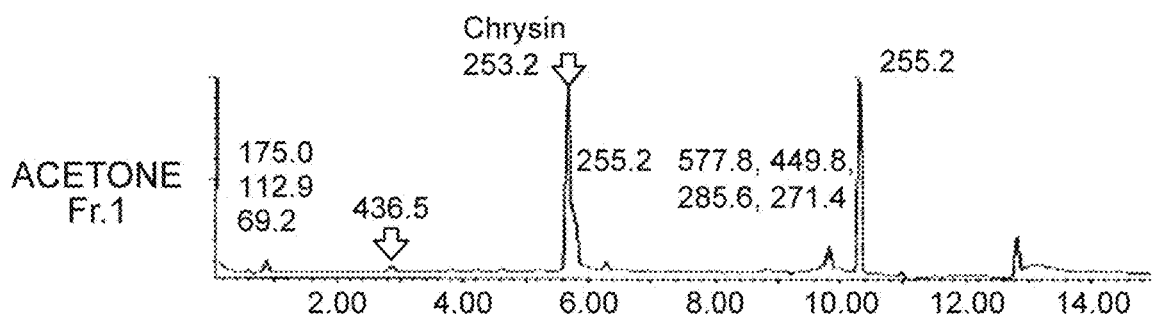
Figure 10:
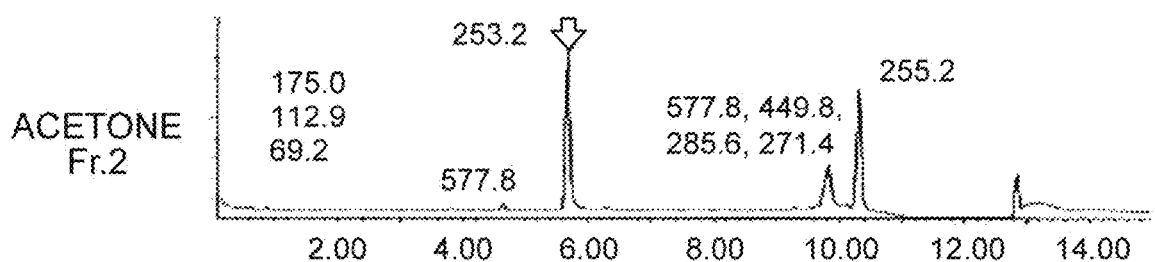

A chart obtained for each fraction is illustrated in FIG. 10(a), FIG. 10(b), and FIG. 10(c). Only the acetone fraction 1 having high antitussive activity had an ultraviolet absorption of 295.8 nm with a retention time of 2.8 minutes, and had a peak having the molecular ion peaks of m/z 438 [M+H] and m/z 436 [M−H]. In addition, the acetone fraction 1 and the acetone fraction 2 included a large amount of chrysin with a retention time of 5.7 minutes.

Test Example 2-3

200.00 g of acacia honey was weighed, and similar to the above-described Test Example 2-2, the honey aqueous solution was allowed to slowly flow 5 times into a column packed with Diaion HP-20, and then, a 50% methanol aqueous solution and methanol were allowed to sequentially flow, for 4 L each, into the above column. 4 L of acetone was allowed to further flow into the column, and ten columns of 100 mL were collected in order from the earliest elution time, and subsequently three columns of 1000 mL were collected. Each of the obtained fractions was set as acetone fractions 1-1 to 1-10, an acetone fraction 2 (50.59 mg), an acetone fraction 3 (5.09 mg), and an acetone fraction 4 (3.48 mg). For the acetone fractions 1-1 to 1-10, the solvent was removed and the honey fractions were obtained respectively.

The honey fraction obtained from the acetone fractions 1-1 to 1-10 was subjected to thin layer chromatographic analysis. 10 mg of each sample dissolved in 1 mL of acetone was spotted twice by using Silica Gel 60F254 plate (0.5 mm). The development was performed with a solvent in which a mixing ratio of chloroform/methanol/acetate is 9/1/1, and after drying, a doragendorf reagent was sprayed on the plate so as to develop the color. As the doragendorf reagent, a solution prepared by mixing 1.7 g of bismuth subnitrate, 5 mL of mixture obtained by mixing 20 mL of acetate, and 80 mL of distilled water, 5 mL of admixture prepared by mixing 40 g of potassium iodide and 100 mL of distilled water, 20 mL of acetate, and 70 mL of distilled water. The Rf value of the spot for which the color development was confirmed for each sample is indicated in Table 1. The acetone fractions 1-7, 1-8, 1-9, and 1-10 had spots at the Rf value of 0 and 0.74. The acetone fractions 1-1, 1-2, 1-3, 1-4, 1-5, and 1-6 have the spot at the Rf value of 0.74, and have no spot at an original point (Rf value of 0). For further examination, six fractions of the acetone fraction 1-1 to 1-6 (acetone fraction 1-1-6 (1.82 mg)) and four fractions of 1-7 to 1-10 (acetone fractions 1-7-10 (21.72 mg)) which represented the similar trend of the development patterns were collectively used.

TABLE 1

| Sample | Acetone fraction | | | | | | | | | |
|---|---|---|---|---|---|---|---|---|---|---|
|  | 1-1 | 1-2 | 1-3 | 1-4 | 1-5 | 1-6 | 1-7 | 1-8 | 1-9 | 1-10 |
| Rf value | 0.74 | 0.74 | 0.74 | 0.74 | 0.74 | 0.74 | 0, 0.74 | 0, 0.74 | 0, 0.74 | 0, 0.74 |

Figure 11:
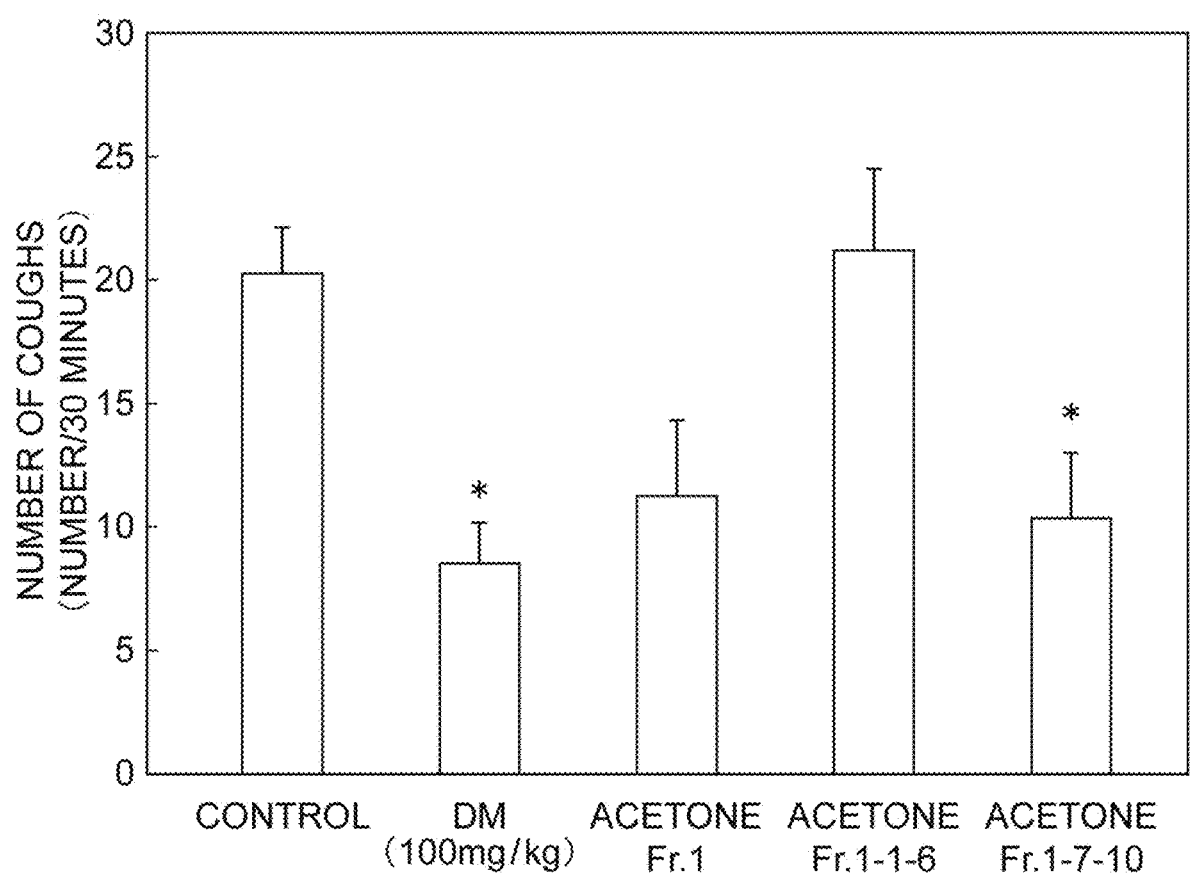
FIG. 11 is a graph illustrating the number of coughs in Test Example 2-3.

An amount equivalent to 2 g/kg of honey of each honey fraction obtained from the acetone fractions 1-1-6, 1-7-10, and the mixture of the acetone fractions 1-1 to 1-10 (acetone fraction 1) was intragastrically administered to the normal guinea pig, and the antitussive action was examined by using the same method as that used in Test Example 2-2. As the control, water or a DM aqueous solution (DM 100 mg/kg) was used instead of the honey fraction aqueous solution. The results are illustrated in FIG. 11 (*: p<0.01). The high antitussive activity was found in the acetone fraction 1-7-10 (0.217 mg/kg). As compared with the honey before the fraction, the specific activity of the honey fraction in the acetone fraction 1-7-10 was 4,630 times. In addition, when LCMS analysis was performed similar to Test Example 2-2, the acetone fraction 1-7-10 had ultraviolet absorption of 295.8 nm with a retention time of 2.8 hours, and had a peak having the molecular ion peaks of m/z 438 [M+H] and m/z 436 [M−H]; whereas the acetone fraction 1-1-6 did not have the peak.

Test Example 2-4

200.00 g of acacia honey was weighed and dissolved in 4 L of water to prepare a honey aqueous solution. The honey aqueous solution was allowed to slowly flow 5 times into a column (φ5×31 cm, 500 mL) packed with Diaion HP-20, then, 4 L of 50% ethanol was allowed to flow into a column. 4 L of ethanol was allowed to further flow into the column and collected by 2 L at a time, then, 4 L of acetone was allowed to flow into the column and collected by 1 L at a time, and they were collected as a 50% ethanol fraction (34.24 g), an ethanol fraction 1 (23.14 mg), an ethanol fraction 2 (12.71 mg), an acetone fraction 1 (16.86) mg, an acetone fraction 2 (26.82 mg), and an acetone fraction 3-4 (6.79 mg), respectively.

The obtained honey fraction obtained by removing a solvent from each of the obtained fractions was dissolved in water, and an amount equivalent to 1 g/kg of honey in each fraction was intragastrically administered to the normal guinea pig. In 30 minutes after administration, a citric acid (0.1 M) was sprayed for 5 minutes, and the number of cough reflexes was counted for 30 minutes immediately after the start of spraying. The antitussive effect, which is weaker than the DM aqueous solution (100 mg/kg), was detected in the ethanol fraction 2 (0.62 mg/kg) and the acetone fraction 1 (0.07 mg/kg) (not shown).

Test Example 3

Test Example 3-1

HPLC fractionation was performed by using 16.96 mg of acetone fraction 1-7-10 obtained in the above-described Test Example 2. As the column, Cosmosil 5C-18-AR-II (φ20 mm×250 mm, manufactured by NACALAI TESQUE) was used. The mobile phase was set as 0.1% TFA water (A) and acetonitrile (B), and a gradient was set as 50% B (0 to 5 minutes), 50 to 100% B (5 to 55 minutes, linear gradient), 100% B (55 to 65 minutes), and 50% B (65 to 75 minutes). Detection was performed under the conditions that the flow rate was set as 10 mL/min, the column temperature was set as 40° C., the injection volume was set as 50 µl, and UV was set to 245 nm. The fractions with the retention times of 0 to 25 minutes (HPLC fraction 1, 1.71 mg), 25 to 54 minutes (HPLC fraction 2, 3.88 mg), 54 minutes (HPLC fraction 3, 1.84 mg), and 54 to 75 minutes (HPLC fraction 4, 4.89 mg) were collected.

The thin layer chromatography analysis was performed on the obtained fraction by two methods. 10 mg of each sample dissolved in 1 mL of acetone was spotted once by using Silica Gel 60F254 plate (0.5 mm). As the first method, the development was performed with a solvent in which a mixing ratio of chloroform/methanol/acetate is 9/1/0.3, and after drying, a doragendorf reagent was sprayed on the plate so as to develop the color similar to Test Example 2-3. The Rf value of the spot for which the color development was confirmed for each sample is indicated in Table 2. The results for the acetone fraction 1 also indicated. In the HPLC fraction 1, it was confirmed that the spot was developed at Rf values of 0 to 0.03, and 0.56. In the HPLC fractions 2 and 3, the spot at Rf values of 0 to 0.03 was not found.

TABLE 2

| Sample | Acetone fraction 1 | HPLC fraction | | | |
|---|---|---|---|---|---|
|  |  | 1 | 2 | 3 | 4 |
| Rf value | 0.56, 0.86 | 0~0.03, 0.56 | 0.56 | 0.86 | 0.86 |

As the second method, the plate in which the sample is spotted similar to above is developed with a solvent in which a mixing ratio of chloroform/methanol/water is 1/1/0.3, and after drying, a ninhydrin reagent was sprayed on the plate and heated at 105° C. so as to develop the color. The Rf value of the spot for which the color development was confirmed for each sample is indicated in Table 3. In the HPLC fraction 1, it was confirmed that the spot was developed at Rf values of 0.06, 0.44, 0.47 and 0.62.

TABLE 3

| Sample | HPLC fraction | | | |
|---|---|---|---|---|
|  | 1 | 2 | 3 | 4 |
| Rf value | 0.06, 0.44, 0.47, 0.62 | 0.86 | 0.86 | 0.86 |

Figure 12:
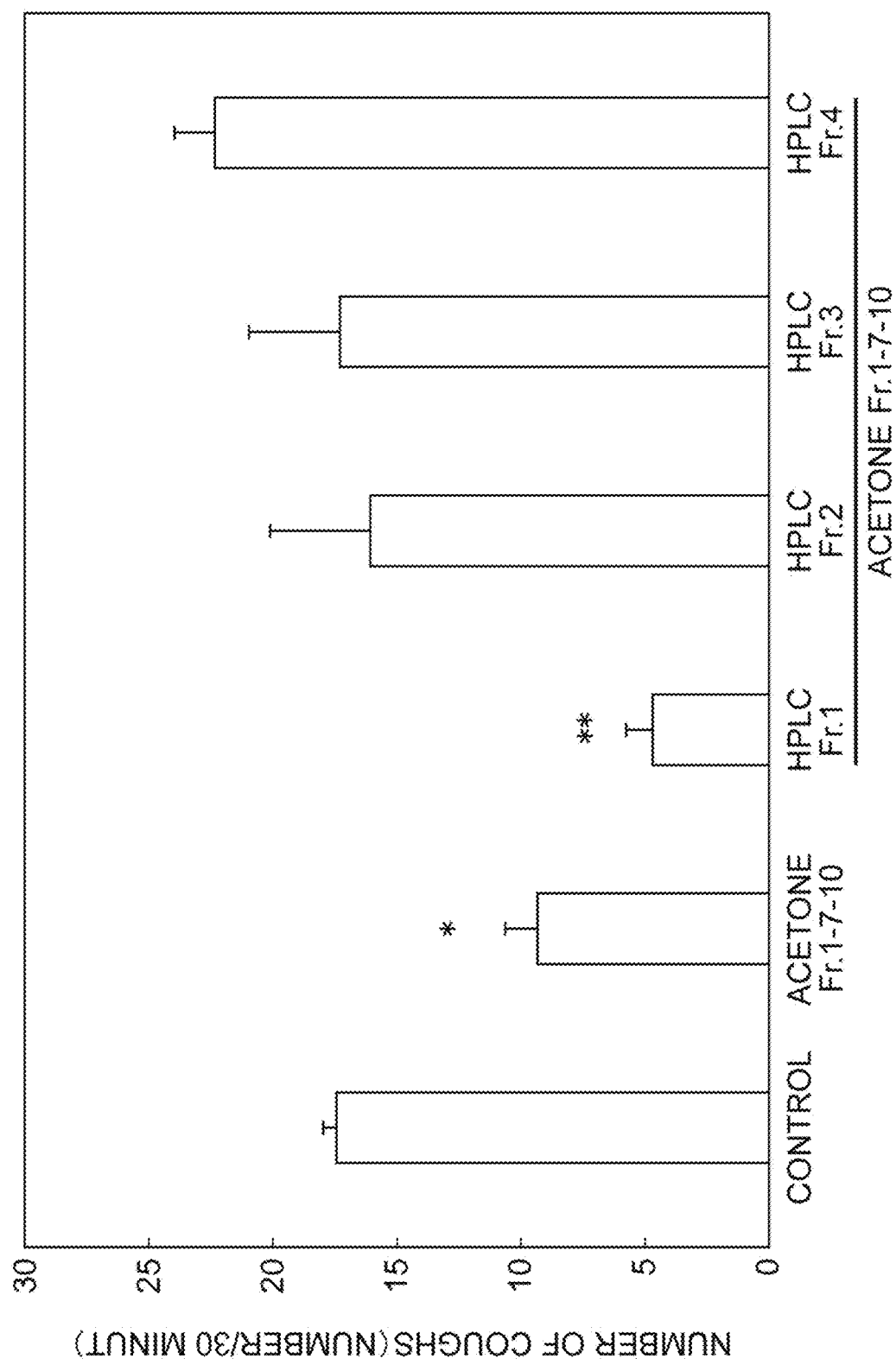
FIG. 12 is a graph illustrating the number of coughs in Test Example 3-1.

An amount equivalent to 2 g/kg of honey of each honey fraction obtained from HPLC fractions 1 to 4, and the acetone fraction 1-7-10 in Test Example 2-3 was intragastrically administered to the normal guinea pig, and the antitussive action was examined by using the same method as that used in Test Example 2-2. As the control, water was used instead of the honey fraction aqueous solution. The results are illustrated in FIG. 12. The high antitussive activity was found in the HPLC fraction 1 (0.017 mg/kg). As compared with the honey before the fraction, the specific activity of the honey fraction in the HPLC fraction 1 was 58,824 times. In addition, when the LCMS analysis was performed similar to Test Example 2, the HPLC fraction 1, has an ultraviolet absorption of 295.8 nm with a retention time of 2.8 minutes, and includes a peak having the molecular ion peaks of m/z 438 [M+H] and m/z 436 [M−H].

Test Example 3-2

The HPLC fractionation was performed by using 14.56 mg of acetone fraction 1-7-10 obtained in the above-described Test Example 2-3 under the same conditions as those of Test Example 3-1 except that the retention time of the fractionation was changed. The fractions with the retention times of 0 to 4 minutes (HPLC fraction 1', 0.29 mg), 4 to 9 minutes (HPLC fraction 2', 1.73 mg), 9 to 12 minutes (HPLC fraction 3', 0.32 mg), 12 to 19 minutes (HPLC fraction 4', 0.91 mg), 20 minutes (HPLC fraction 5', 0.70 mg), 20 to 23 minutes (HPLC fraction 6', 1.27 mg), and 23 to 26 minutes (HPLC fraction 7', 0.79 mg) were collocated.

The thin layer chromatography analysis was performed on the obtained fraction. 10 mg of each sample dissolved in 1 mL of acetone was spotted twice by using Silica Gel 60F254 plate (0.5 mm). The development was performed with a solvent in which a mixing ratio of chloroform/methanol/water is 1/1/0.3, and after drying, the ninhydrin reagent was sprayed on the plate and heated at 105° C. so as to develop the color similar to Test Example 3-1. The Rf value of the spot for which the color development was confirmed for each sample is indicated in Table 4. In the HPLC fraction 1', it was confirmed that the spot was developed at Rf values of 0.05, 0.12, and 0.51.

TABLE 4

| Sample | HPLC fraction | | | | | | |
|---|---|---|---|---|---|---|---|
| | 1' | 2' | 3' | 4' | 5' | 6' | 7' |
| Rf value | 0.05, 0.12, 0.51 | 0.66, 0.78 | 0.06, 0.51, 0.66, 0.78 | 0.06, 0.66, 0.78 | 0.78 | 0.78 | 0.78 |

Figure 13:
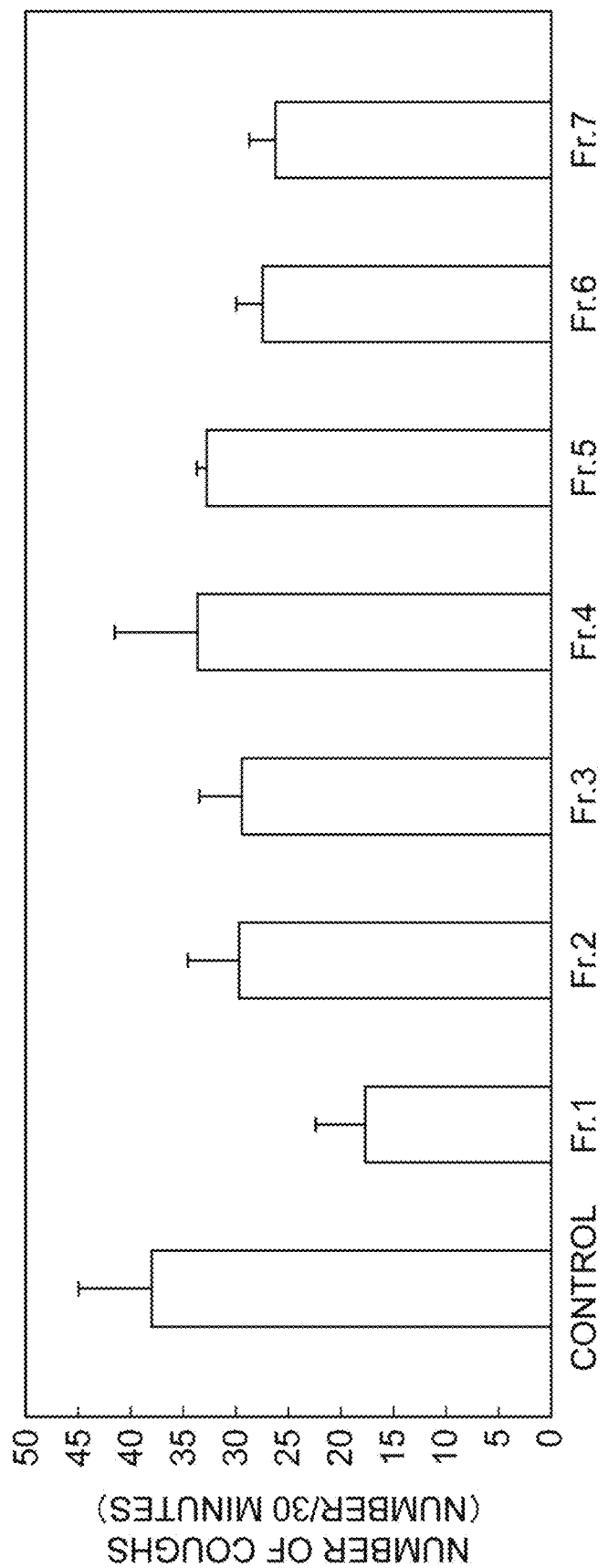
FIG. 13 is a graph illustrating the number of coughs in Test Example 3-2.

An amount equivalent to 2 g/kg of honey of each honey fraction obtained from the HPLC fractions 1' to 7' was intragastrically administered to the normal guinea pig, and the antitussive action was examined by using the same method as that used in Test Example 2-2. As the control, water was used instead of the honey fraction aqueous solution. The results are illustrated in FIG. 13. The high antitussive activity was found in the HPLC fraction 1' (0.0029 mg/kg). As compared with the honey before the fraction, the specific activity of the honey fraction in the HPLC fraction 1' was 322,828 times.

Test Example 4

Test Example 4-1

Figure 14:
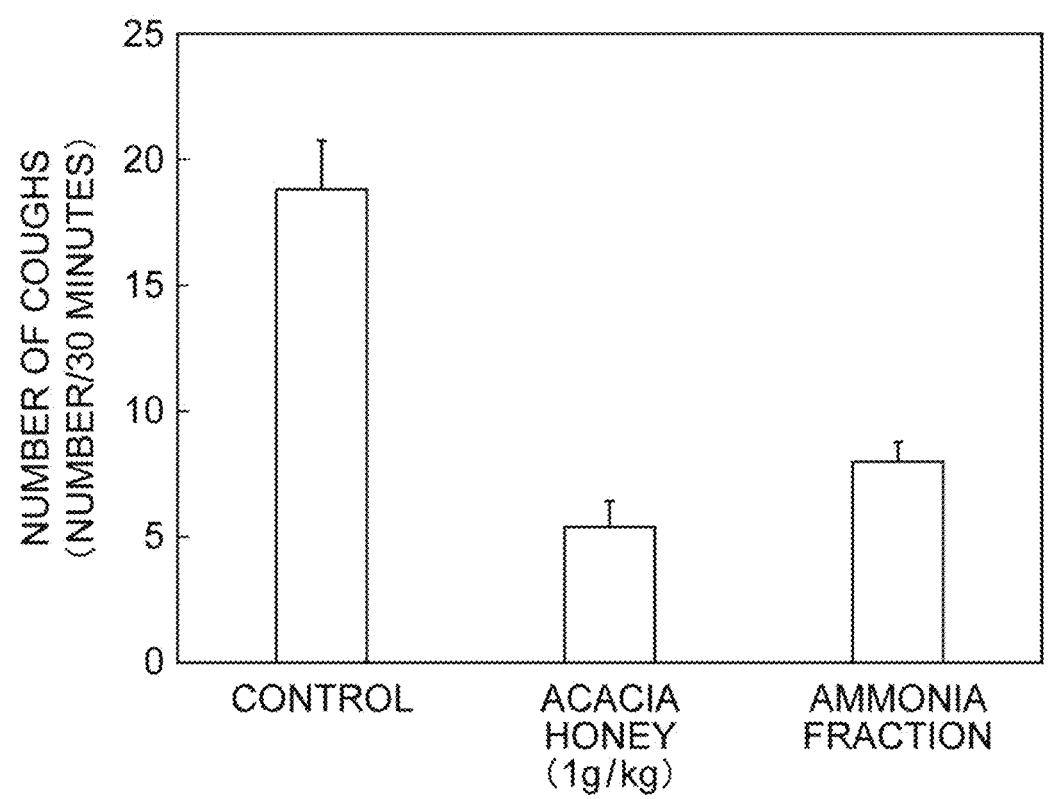
FIG. 14 is a graph illustrating the number of coughs in Test Example 4-1.

90.00 g of acacia honey was diluted with 55 mL of 0.2 M ammonia water and 80 mL of water so as to prepare a honey aqueous solution at pH 9, and the prepared solution was allowed to flow a column packed with a strongly basic anion exchange resin (II type, IRA910CT CL, φ3×13 cm, 90 mL, manufactured by Organo Corporation) conditioned with a 1 M aqueous sodium hydroxide solution and water. Ion exchanged water (1080 mL) and 1 M hydrochloric acid (360 mL) were allowed to sequentially flow into the column. A 1 M hydrochloric acid fraction was collected to flow into a column packed with a strongly acidic cation exchange resin (200CTNA, φ2×15.5 cm, 45 mL, manufactured by Organo Corporation) conditioned with 1 M hydrochloric acid and water. Ion exchanged water (180 mL) and 1 M ammonia water (180 mL) were allowed to sequentially flow into the aforementioned column, and then a 1 M ammonia water fraction (30.76 mg) was collected. The antitussive action was examined with respect to the amount equivalent to 1 g/kg of honey of the obtained honey fractions by using the same method as that used in Test Example 2-2, and as a result, it was confirmed that 1 M ammonia water fraction has high antitussive activity (FIG. 14). As compared with the honey before the fraction, the specific activity of the honey fraction in the 1 M aqueous ammonia water fraction was 3,030 times.

Regarding the 1 M aqueous ammonia water fraction obtained from Test Example 4-1, LCMS analysis was performed under the conditions similar to Test Example 2-2. The 1 M aqueous ammonia water fraction has an ultraviolet absorption of 295.8 nm with a retention time of 2.8 minutes, and includes a peak having the molecular ion peaks of m/z 438 [M+H] and m/z 436 [M−H].

Test Example 4-2

40.00 g of acacia honey was diluted with ion exchanged water (60 mL) so as to prepare a honey aqueous solution at pH 4, and the prepared solution was allowed to flow a column packed with a strongly acidic cation exchange resin (200CTNA, φ2×14.5 cm, 43 mL, manufactured by Organo Corporation) conditioned with 1 M hydrochloric acid and water. Ion exchanged water (344 mL), 0.5M ammonia water (172 mL), and 1 M ammonia water (172 mL) were allowed to sequentially flow into the aforementioned column, and then a 0.5 M ammonia water fraction (1.94 mg) and 1 M ammonia water fraction (62.5 mg) were collected. The antitussive action was examined with respect to the amount equivalent to 1 g/kg of honey of the obtained honey fractions by using the same method as that used in Test Example 2-2, and as a result, it was confirmed that both fractions have high antitussive activity (not shown).

Test Example 5

Test Example 5-1

In order to confirm whether or not the antitussive action of the honey is mediated by the opioid receptor, the effect of naloxone on the antitussive action of the honey was examined.

Figure 15:
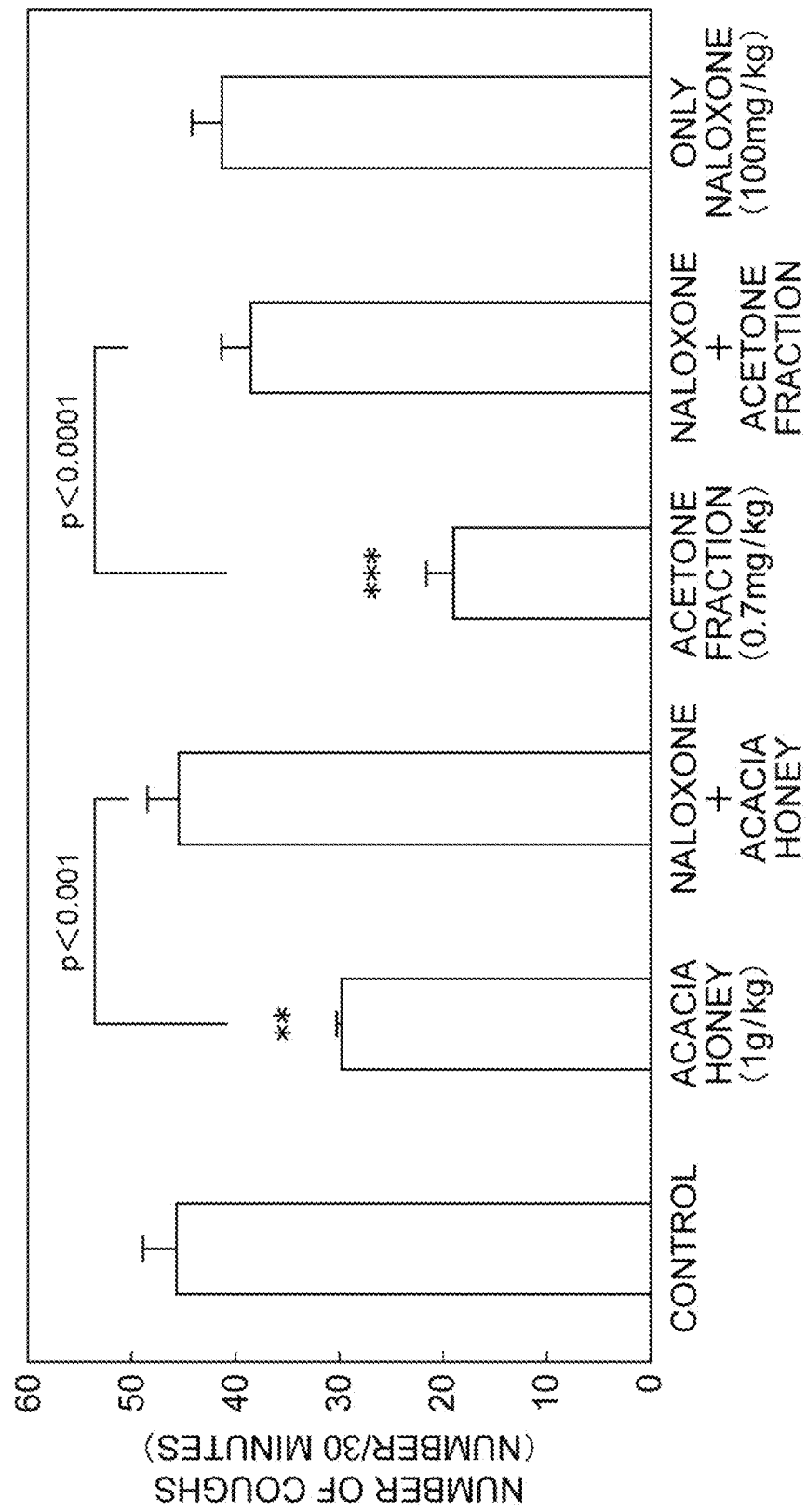
FIG. 15 is a graph illustrating the number of coughs in Test Example 5-1.

The sulfur dioxide gas-exposed guinea pig was used to induce cough with a citric acid (0.1 M). Groups were divided into a group of the guinea pigs to which the acacia honey (1 g/kg) or the acetone fraction obtained in Test Example 2-1 (0.7 mg/kg) was intragastrically administered, a group of the guinea pigs to which the acacia honey (1 g/kg) or the acetone fraction (0.7 mg/kg) was intragastrically administered in 30 minutes after intraperitoneally administering naloxone (0.3 mg/kg), and a group of the guinea pigs to which only water was administered (control). Then, the number of coughs of the guinea pig was measured for each groups. As a result, the number of the coughs of the group of the guinea pigs to which the honey or the acetone fraction was administered was significantly reduced as compared with the control. In contrast, in the group of the guinea pigs to which the honey or the acetone fraction was administered after the administration of naloxone, the number of coughs was the same level as that of the control (FIG. 15).

Test Example 5-2

The effect of the antitussive action was examined by using the same method as that used in Test Example 5-1 except that the honey (1 g/kg) or the acetone fraction (0.7 mg/kg) was substituted with the HPLC fraction 1' (0.0029 mg/kg) obtained in Test Example 3-2. As a result, in the group of the guinea pigs to which the HPLC fraction 1' was intragastrically administered in 30 minutes after intraperitoneally administering naloxone (0.3 mg/kg), it was confirmed that the antitussive action tends to be decreased as compared with a case where naloxone was not used in combination (not shown).

Since the antitussive action of the honey disappeared by intraperitoneally administering naloxone which is an antagonist of the opioid receptor, it was suggested that at least a part of the antitussive action of the honey is an action mediated by the opioid receptor.

The invention claimed is:

1. A dosage form comprising a honey fraction, where the honey fraction is obtainable by a method comprising:
   (a) obtaining an absorbed component by causing honey to be brought into contact with an adsorbent,
   (b) obtaining an organic solvent fraction by eluting the absorbed component with an organic solvent that is acetone, ethyl acetate, or ethanol, and
   (c) obtaining a honey fraction from the organic solvent fraction, wherein the dosage form is selected from the group consisting of an uncoated tablet, a sugar-coated tablet, an effervescent tablet, a film-coated tablet, a chewable tablet, a lozenge, a capsule, a pill, fine granule, granule, emulsion, and injection,
wherein Step (b) further comprises at least one step selected from the group consisting of Step (b-1), Step (b-2), and Step (b-3),
   (b-1) obtaining, as the organic solvent fraction, a fraction which has a spot at a Rf value in a range of 0.49 to 0.55, which is colored with an anisaldehyde sulfuric acid reagent and a spot at a Rf value in a range of 0.56 to 0.62, which is less colored than the aforementioned spot, when the absorbed component eluted with the organic solvent is fractionated by an elution time, and is developed with a solvent in which a mixing ratio of hexane/ethyl acetate is 4/1 in a thin layer chromatography using silica gel,
   (b-2) obtaining, as the organic solvent fraction, a fraction which has spots at a Rf value 0 and in a range of 0.54 to 0.94, which are colored with a doragendorf reagent when the absorbed component eluted with the organic solvent is fractionated by the elution time, and is developed with a solvent in which the mixing ratio of chloroform/methanol/acetate is 9/1/1 in the thin layer chromatography using silica gel,
   (b-3) obtaining, as the organic solvent fraction, a fraction which is detected with a retention time in a range of 2.0 to 4.0 minutes, and has a peak which has molecular ion peaks of m/z438 [M+H] and m/z436 [M−H] in a case where the absorbed component eluted with the organic solvent is fractionated by the elution time, and is measured under the following conditions in liquid chromatography mass spectrometry;
(Measuring Conditions)
   Column: Acquity UPLC BFH C18 (φ2.1×100 mm, manufactured by Waters Corporation)
   Flow rate: 0.4 mL/min
   Column temperature: 40° C.
   Solvent: 5% B (0 to 0.25 min), 5 to 100% B (0.25 to 10 min, linear gradient), 100% B (10 to 12 min), 5% B (12 to 15 min)
   A: 0.05% of formic acid aqueous solution, B: 100% of acetonitrile
   Injection volume: 2 μl.

2. The honey fraction according to claim 1, wherein the absorbed component eluted in Step (b) is a component which is not eluted with water or methanol.

3. The honey fraction according to claim 1, wherein the organic solvent is acetone.

4. The honey fraction according to claim 1, wherein the method further comprises removing a component which is elutable with water from the absorbed component before Step (b).

5. The honey fraction according to claim 1, wherein the method further comprises removing a component which is elutable with methanol, a methanol aqueous solution, or an ethanol aqueous solution from the absorbed component before Step (b).

6. The honey fraction according to claim 1, wherein Step (b) further comprises Step (b-4) obtaining, as the organic solvent fraction, a fraction which satisfies at least one condition of the following conditions (1) and (2) by further fractioning the fraction obtained in Step (b-2) with a reverse phase adsorbent,
   (1) Having a spot at a Rf value in a range of 0 to 0.22, which is colored with a doragendorf reagent when the development is performed with a solvent in which the mixing ratio of chloroform/methanol/acetate is 9/1/0.3 in the thin layer chromatography using silica gel,
   (2) Having at least one spot selected from the group consisting of the spots at Rf values in a range of 0.02 to 0.09, 0.10 to 0.20, and 0.30 to 0.53, which is colored with a ninhydrin reagent when the development is performed with a solvent in which the mixing ratio of chloroform/methanol/water is 1/1/0.3 in the thin layer chromatography using silica gel.

7. A method of activing an opioid comprising administering an effective amount of the honey fraction according to claim 1 to a subject in need thereof.

8. A method of suppressing cough or relieving pain comprising administering an effective amount of the honey fraction according to claim 1 to a subject in need thereof.

* * * * *